United States Patent
Turowska et al.

(10) Patent No.: US 9,791,454 B2
(45) Date of Patent: Oct. 17, 2017

(54) METHOD FOR DIAGNOSING A MOLECULAR PHENOTYPE OF A PATIENT SUFFERING FROM AN ILLNESS ACCOMPANIED BY CHRONIC INFLAMMATION

(71) Applicant: STERNA BIOLOGICALS GMBH & CO. KG, Marburg (DE)

(72) Inventors: Agnieszka Turowska, Giessen (DE); Joachim Bille, Reiskirchen (DE)

(73) Assignee: STERNA BIOLOGICALS GMBH & CO. KG, Marburg (DE)

( * ) Notice: Subject to any disclaimer, the term of this patent is extended or adjusted under 35 U.S.C. 154(b) by 0 days.

(21) Appl. No.: 14/428,043

(22) PCT Filed: Sep. 4, 2013

(86) PCT No.: PCT/EP2013/068317
§ 371 (c)(1),
(2) Date: Mar. 13, 2015

(87) PCT Pub. No.: WO2014/040891
PCT Pub. Date: Mar. 20, 2014

(65) Prior Publication Data
US 2015/0260728 A1 Sep. 17, 2015

(30) Foreign Application Priority Data

Sep. 14, 2012 (EP) .................................... 12184500

(51) Int. Cl.
*C12Q 1/68* (2006.01)
*G01N 33/68* (2006.01)
*C12N 15/113* (2010.01)

(52) U.S. Cl.
CPC ....... *G01N 33/6872* (2013.01); *C12N 15/113* (2013.01); *G01N 33/6893* (2013.01); *C12N 2310/127* (2013.01); *C12N 2320/30* (2013.01); *G01N 2333/4703* (2013.01); *G01N 2333/4706* (2013.01); *G01N 2800/52* (2013.01); *G01N 2800/7095* (2013.01)

(58) Field of Classification Search
CPC ..................................................... C12C 1/68
See application file for complete search history.

(56) References Cited

U.S. PATENT DOCUMENTS

2010/0285154 A1   11/2010   Hwang et al.

FOREIGN PATENT DOCUMENTS

| EP | 2460880 A1 | 6/2012 |
|----|------------|--------|
| WO | WO-2005033314 A2 | 4/2005 |
| WO | WO-2009075822 A1 | 6/2009 |
| WO | WO-2009124090 A1 | 10/2009 |
| WO | WO-2010107957 A2 | 9/2010 |

OTHER PUBLICATIONS

Nakamura et al. (J Allergy Clin Immunol, Feb. 1999: 215-222).*
Zhang et al. (J Allergy Clin Immunol, Nov. 2008: 961-968).*
Wenzel et al., "Evidence That Severe Asthma can be Divided Pathologically into Two Inflammatory Subtypes with Distinct Physiologic and Clinical Characteristics", *Am J Respir Crit Care Med.*, vol. 160, pp. 1001-1008 (1999).
European Supplementary Search Report in European Application No. 12184500.2 dated May 14, 2013.
International Search Report in corresponding PCT/EP2013/068317 dated Dec. 18, 2013.
International Preliminary Report on Patentability in PCT/EP2013/068317 dated Mar. 17, 2015.
Das et al., "A critical role for NF-$_\kappa$B in Gata3 expression and T$_H$2 differentiation in allergic airway inflammation", *Nature Immunology*, vol. 2, No. 1, pp. 45-50 (2001).
Ettreiki C. et al., "Effects of Iron on T-Bet/Gata3 Expression and Epigenetic Regulations in TH1 and TH2 Inflammatory Models", *Inflammation Research*, pp. S48-S49 (2011).
Corren et al., "Lebrikizumab Treatment in Adults with Asthma", *The New England Journal of Medicine*, pp. 1-11 (2011).
Supplementary Appendix to Corren et al., "Lebrikizumab Treatment in Adults with Asthma", *The New England Journal of Medicine*, pp. 1-11 (2011).
Woodruff et al., "Genome-wide profiling identifies epithelial cell genes associated with asthma and with treatment response to corticosteroids", *PNAS*, vol. 104, No. 40, pp. 15858-15863 (2007).
Woodruff et al., "T-helper Type 2-driven Inflammation Defines Major Subphenotypes of Asthma", *Am J Respir Crit Care Med*, vol. 180, pp. 388-395 (2009).

* cited by examiner

*Primary Examiner* — Kimberly Chong
(74) *Attorney, Agent, or Firm* — Marshall, Gerstein & Borun LLP

(57) ABSTRACT

Chronic inflammation is an increasing medical problem area of high socioeconomic significance. The invention relates to a method and a kit for diagnosing a molecular phenotype of a patient suffering from an illness accompanied by chronic inflammation, and to a medicament for treating such a patient. To that end, the gene expression of GATA-3 and/or Tbet in a biological isolate of the patient is measured and used for association with a molecular phenotype of the illness.

6 Claims, 7 Drawing Sheets

SEQUENCE LISTING

<160> NUMBER OF SEQ ID NOS: 155

<210> SEQ ID NO 1
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd1 DNAzyme against GATA-3mRNA

<400> SEQUENCE: 1
tcggtcagag gctagctaca acgatgcgtt gct                          33

<210> SEQ ID NO 2
<211> LENGTH: 33
<212> TYPE: DNA
<213> ORGANISM: Artificial Sequence
<220> FEATURE:
<223> OTHER INFORMATION: DNAzyme against GATA-3 mRNA
<220> FEATURE:
<221> NAME/KEY: misc_feature
<222> LOCATION: (1)..(33)
<223> OTHER INFORMATION: hgd2 DNAzyme against GATA-3 mRNA

<400> SEQUENCE: 2
ggcgtacgag gctagctaca acgactgctc ggt                          33

<210> SEQ ID NO 3
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd3 DNAzyme against GATA-3 mRNA

<400> SEQUENCE: 3
ggcggcgtag gctagctaca acgagacctg ctc                          33

<210> SEQ ID NO 4
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd4 DNAzyme against GATA-3 mRNA

<400> SEQUENCE: 4
ctcgggtcag gctagctaca acgactgggt agc                          33

<210> SEQ ID NO 5
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd5 DNAzyme against GATA-3 mRNA

<400> SEQUENCE: 5
tcctctgcag gctagctaca acgacgggt cct                33

<210> SEQ ID NO 6
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd6 DNAzyme against GATA-3 mRNA

<400> SEQUENCE: 6
actctgcaag gctagctaca acgatctgcg agc                33

<210> SEQ ID NO 7
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd7 DNAzyme against GATA-3 mRNA

<400> SEQUENCE: 7
gggcgacgag gctagctaca acgatctgca att                33

<210> SEQ ID NO 8
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd8 DNAzyme against GATA-3 mRNA

<400> SEQUENCE: 8
aaggggcgag gctagctaca acgagactct gca                33

<210> SEQ ID NO 9
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd9 DNAzyme against GATA-3 mRNA

<400> SEQUENCE: 9
aaaacgggag gctagctaca acgacaggtt gta                33

<210> SEQ ID NO 10
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd10 DNAzyme against GATA-3 mRNA

<400> SEQUENCE: 10
agaataaaag gctagctaca acgagggacc agg					33

<210> SEQ ID NO 11
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd11 DNAzyme against GATA-3 mRNA

<400> SEQUENCE: 11
atggcagaag gctagctaca acgaaaaacg gga					33

<210> SEQ ID NO 12
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd12 DNAzyme against GATA-3 mRNA

<400> SEQUENCE: 12
aactgggtag gctagctaca acgaggcaga ata					33

<210> SEQ ID NO 13
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd13 DNAzyme against GATA-3 mRNA

<400> SEQUENCE: 13
atccaaaaag gctagctaca acgatgggta tgg					33

<210> SEQ ID NO 14
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd14 DNAzyme against GATA-3 mRNA

<400> SEQUENCE: 14
aggggaagag gctagctaca acgaaaaaat cca					33

<210> SEQ ID NO 15
<211> LENGTH: 33
<212> TYPE: DNA
<213> ORGANISM: Artificial Sequence
<220> FEATURE:
<223> OTHER INFORMATION: hgd15 DNAzyme against GATA-3 mRNA
<220> FEATURE:
<221> NAME/KEY: misc_feature
<222> LOCATION: (1)..(33)
<223> OTHER INFORMATION: hgd15 DNAzyme against GATA-3 mRNA

```
<400> SEQUENCE: 15
ttttaaaaag gctagctaca acgatatctt gga                                    33

<210> SEQ ID NO 16
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd16 DNAzyme against GATA-3 mRNA

<400> SEQUENCE: 16 gtgggggag gctagctaca acgagggaag gct                                     33

<210> SEQ ID NO 17
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd17 DNAzyme against GATA-3 mRNA

<400> SEQUENCE: 17
gttgaatgag gctagctaca acgattgctt tcg                                    33

<210> SEQ ID NO 18
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd18 DNAzyme against GATA-3 mRNA

<400> SEQUENCE: 18
gtcgttgaag gctagctaca acgagatttg ctt                                    33

<210> SEQ ID NO 19
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd19 DNAzyme against GATA-3 mRNA

<400> SEQUENCE: 19
ggcccggaag gctagctaca acgaccgcgc gcg                                    33

<210> SEQ ID NO 20
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
```

```
<223> OTHER INFORMATION: hgd20 DNAzyme against GATA-3 mRNA

<400> SEQUENCE: 20
tcacctccag gctagctaca acgaggcctc ggc                         33

<210> SEQ ID NO 21
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd21 DNAzyme against GATA-3 mRNA

<400> SEQUENCE: 21
ccgccgtcag gctagctaca acgactccat ggc                         33

<210> SEQ ID NO 22
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd22 DNAzyme against GATA-3 mRNA

<400> SEQUENCE: 22
ggtggctcag gctagctaca acgaccagcg cgg                         33

<210> SEQ ID NO 23
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd23 DNAzyme against GATA-3 mRNA

<400> SEQUENCE: 23
cgttgagcag gctagctaca acgaggcggg gtg                         33

<210> SEQ ID NO 24
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd24 DNAzyme against GATA-3 mRNA

<400> SEQUENCE: 24
ccgcgtccag gctagctaca acgagtagga gtg                         33

<210> SEQ ID NO 25
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
```

```
<222> LOCATION: (1)..(33)
<223> OTHER INFORMATION: hgd25 DNAzyme against GATA-3 mRNA

<400> SEQUENCE: 25
cagcgggtag gctagctaca acgatgcgcc gcg                                    33

<210> SEQ ID NO 26
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd26 DNAzyme against GATA-3 mRNA

<400> SEQUENCE: 26
gcacatccag gctagctaca acgactcctc cgg                                    33

<210> SEQ ID NO 27
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd27 DNAzyme against GATA-3 mRNA

<400> SEQUENCE: 27
aaaagcacag gctagctaca acgaccacct cct                                    33

<210> SEQ ID NO 28
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd28 DNAzyme against GATA-3 mRNA

<400> SEQUENCE: 28
taaaaagcag gctagctaca acgaatccac ctc                                    33

<210> SEQ ID NO 29
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd29 DNAzyme against GATA-3 mRNA

<400> SEQUENCE: 29
gaccgtcgag gctagctaca acgagttaaa aag                                    33

<210> SEQ ID NO 30
<211> LENGTH: 33
<212> TYPE: DNA
<213> ORGANISM: Artificial Sequence
<220> FEATURE:
<223> OTHER INFORMATION: DNAzyme
<220> FEATURE:
```

<221> NAME/KEY: misc_feature
<222> LOCATION: (1)..(33)
<223> OTHER INFORMATION: hgd30 DNAzyme against GATA-3 mRNA

<400> SEQUENCE: 30
ttgccttgag gctagctaca acgacgtcga tgt        33

<210> SEQ ID NO 31
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd31 DNAzyme against GATA-3 mRNA

<400> SEQUENCE: 31
agggcgggag gctagctaca acgagtggtt gcc        33

<210> SEQ ID NO 32
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd32 DNAzyme against GATA-3 mRNA

<400> SEQUENCE: 32
tggccctgag gctagctaca acgacgagtt tcc        33

<210> SEQ ID NO 33
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd33 DNAzyme against GATA-3 mRNA

<400> SEQUENCE: 33
acctctgcag gctagctaca acgacgtggc cct        33

<210> SEQ ID NO 34
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd34 DNAzyme against GATA-3 mRNA

<400> SEQUENCE: 34
cggagggtag gctagctaca acgactctgc acc        33

<210> SEQ ID NO 35
<211> LENGTH: 33
<212> TYPE: DNA
<213> ORGANISM: Artificial Sequence
<220> FEATURE:
<223> OTHER INFORMATION: DNAzyme

```
<220> FEATURE:
<221> NAME/KEY: misc_feature
<222> LOCATION: (1)..(33)
<223> OTHER INFORMATION: hgd35 DNAzyme against GATA-3 mRNA

<400> SEQUENCE: 35
ggcggcacag gctagctaca acgactggct ccc                                   33

<210> SEQ ID NO 36
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd36 DNAzyme against GATA-3 mRNA

<400> SEQUENCE: 36
cgggcggcag gctagctaca acgaacctgg ctc                                   33

<210> SEQ ID NO 37
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd37 DNAzyme against GATA-3mRNA

<400> SEQUENCE: 37
agggatccag gctagctaca acgagaagca gag                                   33

<210> SEQ ID NO 38
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd38 DNAzyme against GATA-3 mRNA

<400> SEQUENCE: 38
gggtagggag gctagctaca acgaccatga agc                                   33

<210> SEQ ID NO 39
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd39 DNAzyme against GATA-3 mRNA

<400> SEQUENCE: 39
gggctgagag gctagctaca acgatccagg ggg                                   33

<210> SEQ ID NO 40
<211> LENGTH: 33
<212> TYPE: DNA
<213> ORGANISM: Artificial Sequence
<220> FEATURE:
```

<223> OTHER INFORMATION: DNAzyme
<220> FEATURE:
<221> NAME/KEY: misc_feature
<222> LOCATION: (1)..(33)
<223> OTHER INFORMATION: hgd40 DNAzyme against GATA-3 mRNA

<400> SEQUENCE: 40
gtggatggag gctagctaca acgagtcttg gag                                   33

<210> SEQ ID NO 41
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd41 DNAzyme against GATA-3 mRNA

<400> SEQUENCE: 41
cgtggtggag gctagctaca acgaggacgt ctt                                   33

<210> SEQ ID NO 42
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd42 DNAzyme against GATA-3 mRNA

<400> SEQUENCE: 42
gggggtagag gctagctaca acgaggagag ggg                                   33

<210> SEQ ID NO 43
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd43 DNAzyme against GATA-3 mRNA

<400> SEQUENCE: 43
ggaggaggag gctagctaca acgagaggcc ggg                                   33

<210> SEQ ID NO 44
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd44 DNAzyme against GATA-3 mRNA

<400> SEQUENCE: 44
gccccccgag gctagctaca acgaaaggag gag                                   33

<210> SEQ ID NO 45
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd45 DNAzyme against GATA-3 mRNA

<400> SEQUENCE: 45
ccggggagag gctagctaca acgagtcctt cgg                                    33

<210> SEQ ID NO 46
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd46 DNAzyme against GATA-3 mRNA

<400> SEQUENCE: 46
ggacagcgag gctagctaca acgagggtcc ggg                                    33

<210> SEQ ID NO 47
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd47 DNAzyme against GATA-3 mRNA

<400> SEQUENCE: 47
tggggtggag gctagctaca acgaagcgat ggg                                    33

<210> SEQ ID NO 48
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd48 DNAzyme against GATA-3 mRNA

<400> SEQUENCE: 48
cttgaggcag gctagctaca acgatctttc tcg                                    33

<210> SEQ ID NO 49
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd49 DNAzyme against GATA-3 mRNA

<400> SEQUENCE: 49
cacctggtag gctagctaca acgattgagg cac                                    33

<210> SEQ ID NO 50
<211> LENGTH: 33
<212> TYPE: DNA

```
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd50 DNAzyme against GATA-3 mRNA

<400> SEQUENCE: 50
gcaggggcag gctagctaca acgactggta ctt                                    33

<210> SEQ ID NO 51
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd51 DNAzyme against GATA-3 mRNA

<400> SEQUENCE: 51
ccagcttcag gctagctaca acgagctgtc ggg                                    33

<210> SEQ ID NO 52
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd52 DNAzyme against GATA-3 mRNA

<400> SEQUENCE: 52
gtgggacgag gctagctaca acgatccagc ttc                                    33

<210> SEQ ID NO 53
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd53 DNAzyme against GATA-3 mRNA

<400> SEQUENCE: 53
ggagtgggag gctagctaca acgagactcc agc                                    33

<210> SEQ ID NO 54
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd54 DNAzyme against GATA-3 mRNA

<400> SEQUENCE: 54
atgctgccag gctagctaca acgagggagt ggg                                    33

<210> SEQ ID NO 55
<211> LENGTH: 33
```

```
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd55 DNAzyme against GATA-3 mRNA

<400> SEQUENCE: 55
gggcggtcag gctagctaca acgagctgcc acg                                  33

<210> SEQ ID NO 56
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd56 DNAzyme against GATA-3 mRNA

<400> SEQUENCE: 56
gaggctccag gctagctaca acgaccaggg cgg                                  33

<210> SEQ ID NO 57
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd57 DNAzyme against GATA-3 mRNA

<400> SEQUENCE: 57
gtgggtcgag gctagctaca acgagaggag gct                                  33

<210> SEQ ID NO 58
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd58 DNAzyme against GATA-3 mRNA

<400> SEQUENCE: 58
aggtggtgag gctagctaca acgaggggtg gtg                                  33

<210> SEQ ID NO 59
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd59 DNAzyme against GATA-3 mRNA

<400> SEQUENCE: 59
actcgggcag gctagctaca acgagtaggg cgg                                  33

<210> SEQ ID NO 60
```

```
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd60 DNAzyme against GATA-3 mRNA

<400> SEQUENCE: 60
ggagctgtag gctagctaca acgatcgggc acg                                 33

<210> SEQ ID NO 61
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd61 DNAzyme against GATA-3 mRNA

<400> SEQUENCE: 61
ggacttgcag gctagctaca acgaccgaag ccg                                 33

<210> SEQ ID NO 62
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd62 DNAzyme against GATA-3 mRNA

<400> SEQUENCE: 62
gggcctggag gctagctaca acgattgcat ccg                                 33

<210> SEQ ID NO 63
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd63 DNAzyme against GATA-3 mRNA

<400> SEQUENCE: 63
tgtgctggag gctagctaca acgacgggcc ttg                                 33

<210> SEQ ID NO 64
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd64 DNAzyme against GATA-3 mRNA

<400> SEQUENCE: 64
gttcacacag gctagctaca acgatccctg cct                                 33
```

```
<210> SEQ ID NO 65
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd65 DNAzyme against GATA-3 mRNA

<400> SEQUENCE: 65
cagttcacag gctagctaca acgaactccc tgc                                  33

<210> SEQ ID NO 66
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd66 DNAzyme against GATA-3 mRNA

<400> SEQUENCE: 66
cacagttcag gctagctaca acgaacactc cct                                  33

<210> SEQ ID NO 67
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd67 DNAzyme against GATA-3 mRNA

<400> SEQUENCE: 67
gttgccccag gctagctaca acgaagttca cac                                  33

<210> SEQ ID NO 68
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd68 DNAzyme against GATA-3 mRNA

<400> SEQUENCE: 68
tcgccgccag gctagctaca acgaagtggg gtc                                  33

<210> SEQ ID NO 69
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd69 DNAzyme against GATA-3mRNA

<400> SEQUENCE: 69
cccgtgccag gctagctaca acgactcgcc gcc                                  33
```

```
<210> SEQ ID NO 70
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: hgd70 DNAzyme against GATA-3 mRNA

<400> SEQUENCE: 70
ggcgttgcag gctagctaca acgaaggtag tgt                                    33

<210> SEQ ID NO 71
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td21 DNAzyme against T-bet mRNA

<400> SEQUENCE: 71
tggcttctag gctagctaca acgagccctc gtc                                    33

<210> SEQ ID NO 72
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td2 DNAzyme against T-bet mRNA

<400> SEQUENCE: 72
gggctctgag gctagctaca acgagcctgg ctt                                    33

<210> SEQ ID NO 73
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td3 DNAzyme against T-bet mRNA

<400> SEQUENCE: 73
gggaccccag gctagctaca acgacggagc ccg                                    33

<210> SEQ ID NO 74
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td4 DNAzyme against T-bet mRNA

<400> SEQUENCE: 74
ggtgggggag gctagctaca acgacccacc gga                                    33
```

<210> SEQ ID NO 75
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td5 DNAzyme against T-bet mRNA

<400> SEQUENCE: 75 ggcggggag gctagctaca acgaccgagg gcc                     33

<210> SEQ ID NO 76
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td6 DNAzyme against T-bet mRNA

<400> SEQUENCE: 76
gggctgggag gctagctaca acgagggcag gga                    33

<210> SEQ ID NO 77
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td7 DNAzyme against T-bet mRNA

<400> SEQUENCE: 77
cgtcgaggag gctagctaca acgaccgccc ctc                    33

<210> SEQ ID NO 78
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td8 DNAzyme against T-bet mRNA

<400> SEQUENCE: 78
gggctggcag gctagctaca acgacttccc gta                    33

<210> SEQ ID NO 79
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td9 DNAzyme against T-bet mRNA

<400> SEQUENCE: 79
cgatgcccag gctagctaca acgaccgggg cgg         33

<210> SEQ ID NO 80
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td10 DNAzyme against T-bet mRNA

<400> SEQUENCE: 80
gctccacgag gctagctaca acgagcccat ccg         33

<210> SEQ ID NO 81
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td11 DNAzyme against T-bet mRNA

<400> SEQUENCE: 81
ccggctccag gctagctaca acgagatgcc cat         33

<210> SEQ ID NO 82
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td12 DNAzyme against T-bet mRNA

<400> SEQUENCE: 82
tctccgcaag gctagctaca acgaccggct cca         33

<210> SEQ ID NO 83
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td13 DNAzyme against T-bet mRNA

<400> SEQUENCE: 83
ccgtcagcag gctagctaca acgagtctcc gca         33

<210> SEQ ID NO 84
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td14 DNAzyme against T-bet mRNA

<400> SEQUENCE: 84

-continued tccccggcag gctagctaca acgacggctc ggt					33

<210> SEQ ID NO 85
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td15 DNAzyme against T-bet mRNA

<400> SEQUENCE: 85
cccccgcgag gctagctaca acgagctcgt ccg					33

<210> SEQ ID NO 86
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td16 DNAzyme against T-bet mRNA

<400> SEQUENCE: 86
gtagggagag gctagctaca acgacccagg ctg					33

<210> SEQ ID NO 87
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td17 DNAzyme against T-bet mRNA

<400> SEQUENCE: 87
gggcgggcag gctagctaca acgacaaggc gcc					33

<210> SEQ ID NO 88
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td18 DNAzyme against T-bet mRNA

<400> SEQUENCE: 88
cgggaaggag gctagctaca acgatcgccc gcg					33

<210> SEQ ID NO 89
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td19 DNAzyme against T-bet mRNA

<400> SEQUENCE: 89
tagtcctcag gctagctaca acgagcggcc ccg         33

<210> SEQ ID NO 90
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td20 DNAzyme against T-bet mRNA

<400> SEQUENCE: 90
tccccgacag gctagctaca acgactccag tcc         33

<210> SEQ ID NO 91
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td21 DNAzyme against T-bet mRNA

<400> SEQUENCE: 91
tttccccgag gctagctaca acgaacctcc agt         33

<210> SEQ ID NO 92
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td22 DNAzyme against T-bet mRNA

<400> SEQUENCE: 92
tgagcgcgag gctagctaca acgacctcag ttt         33

<210> SEQ ID NO 93
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td23 DNAzyme against T-bet mRNA

<400> SEQUENCE: 93
ggaccacaag gctagctaca acgaaggtgg ttg         33

<210> SEQ ID NO 94
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td24 DNAzyme against T-bet mRNA

<400> SEQUENCE: 94
cttggaccag gctagctaca acgaaacagg tgg                          33

<210> SEQ ID NO 95
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td25 DNAzyme against T-bet mRNA

<400> SEQUENCE: 95
aaacttggag gctagctaca acgacacaac agg                          33

<210> SEQ ID NO 96
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td26 DNAzyme against T-bet mRNA

<400> SEQUENCE: 96
ctgattaaag gctagctaca acgattggac cac                          33

<210> SEQ ID NO 97
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td27 DNAzyme against T-bet mRNA

<400> SEQUENCE: 97
tggtgctgag gctagctaca acgataaact tgg                          33

<210> SEQ ID NO 98
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td28 DNAzyme against T-bet mRNA

<400> SEQUENCE: 98
tgatgatcag gctagctaca acgactctgt ctg                          33

<210> SEQ ID NO 99
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)

<223> OTHER INFORMATION: td29 DNAzyme against T-bet mRNA

<400> SEQUENCE: 99
tggtgatgag gctagctaca acgacatctc tgt        33

<210> SEQ ID NO 100
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td30 DNAzyme against T-bet mRNA

<400> SEQUENCE: 100
gcttggtgag gctagctaca acgagatcat ctc        33

<210> SEQ ID NO 101
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td31 DNAzyme against T-bet mRNA

<400> SEQUENCE: 101
atgggaacag gctagctaca acgaccgccg tcc        33

<210> SEQ ID NO 102
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td32 DNAzyme against T-bet mRNA

<400> SEQUENCE: 102
gaatgggaag gctagctaca acgaatccgc cgt        33

<210> SEQ ID NO 103
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td33 DNAzyme against T-bet mRNA

<400> SEQUENCE: 103
tgacaggaag gctagctaca acgagggaac atc        33

<210> SEQ ID NO 104
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature

```
<222> LOCATION: (1)..(33)
<223> OTHER INFORMATION: td34 DNAzyme against T-bet mRNA

<400> SEQUENCE: 104
agtaaatgag gctagctaca acgaaggaat ggg                                33

<210> SEQ ID NO 105
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td35 DNAzyme against T-bet mRNA

<400> SEQUENCE: 105
cacagtaaag gctagctaca acgagacagg aat                                33

<210> SEQ ID NO 106
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td36 DNAzyme against T-bet mRNA

<400> SEQUENCE: 106
gcccggccag gctagctaca acgaagtaaa tga                                33

<210> SEQ ID NO 107
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td37 DNAzyme against T-bet mRNA

<400> SEQUENCE: 107
ccacaaacag gctagctaca acgacctgta gtg                                33

<210> SEQ ID NO 108
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td38 DNAzyme against T-bet mRNA

<400> SEQUENCE: 108
gtccacaaag gctagctaca acgaatcctg tag                                33

<210> SEQ ID NO 109
<211> LENGTH: 33
<212> TYPE: DNA
<213> ORGANISM: Artificial Sequence
<220> FEATURE:
<223> OTHER INFORMATION: DNAzyme
<220> FEATURE:
```

<221> NAME/KEY: misc_feature
<222> LOCATION: (1)..(33)
<223> OTHER INFORMATION: td39 DNAzyme against T-bet mRNA

<400> SEQUENCE: 109
ccacgtccag gctagctaca acgaaaacat cct         33

<210> SEQ ID NO 110
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td40 DNAzyme against T-bet mRNA

<400> SEQUENCE: 110
ccaagaccag gctagctaca acgagtccac aaa         33

<210> SEQ ID NO 111
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td41 DNAzyme against T-bet mRNA

<400> SEQUENCE: 111
ccaccaagag gctagctaca acgacacgtc cac         33

<210> SEQ ID NO 112
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td42 DNAzyme against T-bet mRNA

<400> SEQUENCE: 112
gctggtccag gctagctaca acgacaagac cac         33

<210> SEQ ID NO 113
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td43 DNAzyme against T-bet mRNA

<400> SEQUENCE: 113
gctctggtag gctagctaca acgacgccag tgg         33

<210> SEQ ID NO 114
<211> LENGTH: 33
<212> TYPE: DNA
<213> ORGANISM: Artificial Sequence
<220> FEATURE:
<223> OTHER INFORMATION: DNAzyme

```
<220> FEATURE:
<221> NAME/KEY: misc_feature
<222> LOCATION: (1)..(33)
<223> OTHER INFORMATION: td44 DNAzyme against T-bet mRNA

<400> SEQUENCE: 114
ctgcacccag gctagctaca acgattgccg ctc                          33

<210> SEQ ID NO 115
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td45 DNAzyme against T-bet mRNA

<400> SEQUENCE: 115
cacactgcag gctagctaca acgaccactt gcc                          33

<210> SEQ ID NO 116
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td46 DNAzyme against T-bet mRNA

<400> SEQUENCE: 116
ctttccacag gctagctaca acgatgcacc cac                          33

<210> SEQ ID NO 117
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td47 DNAzyme against T-bet mRNA

<400> SEQUENCE: 117
gcctttccag gctagctaca acgaactgca ccc                          33

<210> SEQ ID NO 118
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td48 DNAzyme against T-bet mRNA

<400> SEQUENCE: 118
ttcctggcag gctagctaca acgagctgcc ctc                          33

<210> SEQ ID NO 119
<211> LENGTH: 33
<212> TYPE: DNA
<213> ORGANISM: Artificial Sequence
<220> FEATURE:
```

<223> OTHER INFORMATION: DNAzyme
<220> FEATURE:
<221> NAME/KEY: misc_feature
<222> LOCATION: (1)..(33)
<223> OTHER INFORMATION: td49 DNAzyme against T-bet mRNA

<400> SEQUENCE: 119
gtggacgtag gctagctaca acgaaggcgg ttt                               33

<210> SEQ ID NO 120
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td50 DNAzyme against T-bet mRNA

<400> SEQUENCE: 120
ccgggtggag gctagctaca acgagtacag gcg                               33

<210> SEQ ID NO 121
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td51 DNAzyme against T-bet mRNA

<400> SEQUENCE: 121
cctggcgcag gctagctaca acgaccagtg cgc                               33

<210> SEQ ID NO 122
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td52 DNAzyme against T-bet mRNA

<400> SEQUENCE: 122
caaatgaaag gctagctaca acgattcctg gcg                               33

<210> SEQ ID NO 123
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td53 DNAzyme against T-bet mRNA

<400> SEQUENCE: 123
tttcccaaag gctagctaca acgagaaact tcc                               33

<210> SEQ ID NO 124
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td54 DNAzyme against T-bet mRNA

<400> SEQUENCE: 124
attgttggag gctagctaca acgagccccc ttg          33

<210> SEQ ID NO 125
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td55 DNAzyme against T-bet mRNA

<400> SEQUENCE: 125
tgggtcacag gctagctaca acgatgttgg acg          33

<210> SEQ ID NO 126
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td56 DNAzyme against T-bet mRNA

<400> SEQUENCE: 126
tctgggtcag gctagctaca acgaattgtt gga          33

<210> SEQ ID NO 127
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td57 DNAzyme against T-bet mRNA

<400> SEQUENCE: 127
gcacaatcag gctagctaca acgactgggt cac          33

<210> SEQ ID NO 128
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td58 DNAzyme against T-bet mRNA

<400> SEQUENCE: 128
ggagcacaag gctagctaca acgacatctg ggt          33

<210> SEQ ID NO 129
<211> LENGTH: 33
<212> TYPE: DNA

<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td59 DNAzyme against T-bet mRNA

<400> SEQUENCE: 129
actggagcag gctagctaca acgaaatcat ctg         33

<210> SEQ ID NO 130
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td60 DNAzyme against T-bet mRNA

<400> SEQUENCE: 130
atggagggag gctagctaca acgatggagc aca         33

<210> SEQ ID NO 131
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td61 DNAzyme against T-bet mRNA

<400> SEQUENCE: 131
tggtacttag gctagctaca acgaggaggg act         33

<210> SEQ ID NO 132
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td62 DNAzyme against T-bet mRNA

<400> SEQUENCE: 132
gggctggtag gctagctaca acgattatgg agg         33

<210> SEQ ID NO 133
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td63 DNAzyme against T-bet mRNA

<400> SEQUENCE: 133
tcaacgatag gctagctaca acgagcagcc ggg         33

<210> SEQ ID NO 134
<211> LENGTH: 33

```
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td64 DNAzyme against T-bet mRNA

<400> SEQUENCE: 134
cctcaacgag gctagctaca acgaatgcag ccg                             33

<210> SEQ ID NO 135
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td65 DNAzyme against T-bet mRNA

<400> SEQUENCE: 135
tcacctcaag gctagctaca acgagatatg cag                             33

<210> SEQ ID NO 136
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td66 DNAzyme against T-bet mRNA

<400> SEQUENCE: 136
cgtcgttcag gctagctaca acgactcaac gat                             33

<210> SEQ ID NO 137
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td67 DNAzyme against T-bet mRNA

<400> SEQUENCE: 137
gtaaagatag gctagctaca acgagcgtgt tgg                             33

<210> SEQ ID NO 138
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td68 DNAzyme against T-bet mRNA

<400> SEQUENCE: 138
aagtaaagag gctagctaca acgaatgcgt gtt                             33

<210> SEQ ID NO 139
```

```
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td69 DNAzyme against T-bet mRNA

<400> SEQUENCE: 139
ggcaatgaag gctagctaca acgatgggtt tct                               33

<210> SEQ ID NO 140
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td70 DNAzyme against T-bet mRNA

<400> SEQUENCE: 140
tcacggcaag gctagctaca acgagaactg ggt                               33

<210> SEQ ID NO 141
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td71 DNAzyme against T-bet mRNA

<400> SEQUENCE: 141
aggcagtcag gctagctaca acgaggcaat gaa                               33

<210> SEQ ID NO 142
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td72 DNAzyme against T-bet mRNA

<400> SEQUENCE: 142
atctcggcag gctagctaca acgatctggt agg                               33

<210> SEQ ID NO 143
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td73 DNAzyme against T-bet mRNA

<400> SEQUENCE: 143
gctgagtaag gctagctaca acgactcggc att                               33
```

<210> SEQ ID NO 144
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td74 DNAzyme against T-bet mRNA

<400> SEQUENCE: 144
tattatcaag gctagctaca acgatttcag ctg                           33

<210> SEQ ID NO 145
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td75 DNAzyme against T-bet mRNA

<400> SEQUENCE: 145
gggttattag gctagctaca acgacaattt tca                           33

<210> SEQ ID NO 146
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td76 DNAzyme against T-bet mRNA

<400> SEQUENCE: 146
aaggggttag gctagctaca acgatatcaa ttt                           33

<210> SEQ ID NO 147
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td77 DNAzyme against T-bet mRNA

<400> SEQUENCE: 147
ctcccggaag gctagctaca acgacctttg gca                           33

<210> SEQ ID NO 148
<211> LENGTH: 33
<212> TYPE: DNA
<213> ORGANISM: Artificial Sequence
<220> FEATURE:
<223> OTHER INFORMATION: DNAzyme
<220> FEATURE:
<221> NAME/KEY: misc_feature
<222> LOCATION: (1)..(33)
<223> OTHER INFORMATION: td78 DNAzyme against T-bet mRNA

<400> SEQUENCE: 148
gtacatggag gctagctaca acgatcaaag ttc                           33

<210> SEQ ID NO 149
<211> LENGTH: 2588
<212> TYPE: DNA
<213> ORGANISM: Homo sapiens
<220> FEATURE:
<221> NAME/KEY: gene
<222> LOCATION: (1)..(2588)
<223> OTHER INFORMATION: Seq1 T-bet
<220> FEATURE:
<221> NAME/KEY: misc_feature
<222> LOCATION: (952)..(970)
<223> OTHER INFORMATION: td54 bindingsite
<220> FEATURE:
<221> NAME/KEY: misc_feature
<222> LOCATION: (1096)..(1114)
<223> OTHER INFORMATION: td69 bindingsite
<220> FEATURE:
<221> NAME/KEY: misc_feature
<222> LOCATION: (1100)..(1118)
<223> OTHER INFORMATION: td70 bindingsite

<400> SEQUENCE: 149

| | | | | | | |
|---|---|---|---|---|---|---|
| cggcccgctg | gagaggaagc | ccgagagctg | ccgcgcgcct | gccggacgag | ggcgtagaag | 60 |
| ccaggcgtca | gagcccgggc | tccggtgggg | tcccccaccc | ggccctcggg | tccccgccc | 120 |
| cctgctccct | gcccatccca | gcccacgcga | ccctctcgcg | cgcggagggg | cgggtcctcg | 180 |
| acggctacgg | gaaggtgcca | gcccgccccg | gatgggcatc | gtggagccgg | gttgcggaga | 240 |
| catgctgacg | gcaccgagc | cgatgccggg | gagcgacgag | ggccgggcgc | ctggcgccga | 300 |
| cccgcagcac | cgctacttct | acccggagcc | gggcgcgcag | gacgcggacg | agcgtcgcgg | 360 |
| gggcggcagc | ctggggtctc | cctacccggg | gggcgccttg | gtgcccgccc | cgccgagccg | 420 |
| cttccttgga | gcctacgcct | acccgccgcg | accccaggcg | gccggcttcc | ccggcgcggg | 480 |
| cgagtccttc | ccgccgcccg | cggacgccga | gggctaccag | ccgggcgagg | gctacgccgc | 540 |
| cccggacccg | cgcgccgggc | tctacccggg | gccgcgtgag | gactacgcgc | tacccgcggg | 600 |
| actggaggtg | tcgggaaac | tgagggtcgc | gctcaacaac | cacctgttgt | ggtccaagtt | 660 |
| taatcagcac | cagacagaga | tgatcatcac | caagcaggga | cggcggatgt | tcccattcct | 720 |
| gtcatttact | gtgccgggc | tggagcccac | cagccactac | aggatgtttg | tggacgtggt | 780 |
| cttggtggac | cagcaccact | ggcggtacca | gagcggcaag | tgggtgcagt | gtggaaaggc | 840 |
| cgagggcagc | atgccaggaa | accgcctgta | cgtccaccg | gactccccca | acacaggagc | 900 |
| gcactggatg | cgccaggaag | tttcatttgg | gaaactaaag | ctcacaaaca | acaaggggc | 960 |
| gtccaacaat | gtgacccaga | tgattgtgct | ccagtccctc | cataagtacc | agccccggct | 1020 |
| gcatatcgtt | gaggtgaacg | acggagagcc | agaggcagcc | tgcaacgctt | ccaacacgca | 1080 |
| tatctttact | ttccaagaaa | cccagttcat | tgccgtgact | gcctaccaga | atgccgagat | 1140 |
| tactcagctg | aaaattgata | ataccccctt | tgccaaagga | ttccgggaga | ctttgagtc | 1200 |
| catgtacaca | tctgttgaca | ccagcatccc | ctccccgcct | ggacccaact | gtcaattcct | 1260 |
| tgggggagat | cactactctc | ctctcctacc | caaccagtat | cctgttccca | gccgcttcta | 1320 |
| ccccgacctt | cctggccagg | cgaaggatgt | ggttcccag | gcttactggc | tgggggcccc | 1380 |
| ccgggaccac | agctatgagg | ctgagtttcg | agcagtcagc | atgaagcctg | cattcttgcc | 1440 |
| ctctgcccct | gggcccacca | tgtcctacta | ccgaggccag | gaggtcctgg | cacctggagc | 1500 |
| tggctggcct | gtggcacccc | agtaccctc | caagatgggc | ccggccagct | ggttccgccc | 1560 |
| tatgcggact | ctgcccatgg | aacccggccc | tggaggctca | gagggacggg | gaccagagga | 1620 |
| ccagggtccc | cccttggtgt | ggactgagat | tgcccccatc | cggccggaat | ccagtgattc | 1680 |

-continued

```
aggactgggc gaaggagact ctaagaggag gcgcgtgtcc ccctatcctt ccagtggtga    1740
cagctcctcc cctgctgggg ccccttctcc ttttgataag gaagctgaag gacagtttta    1800
taactatttt cccaactgag cagatgacat gatgaaagga acagaaacag tgttattagg    1860
ttggaggaca ccgactaatt tgggaaacgg atgaaggact gagaaggccc ccgctccctc    1920
tggcccttct ctgtttagta gttggttggg gaagtggggc tcaagaagga ttttggggtt    1980
caccagatgc ttcctggccc acgatgaaac ctgagagggg tgtccccttg ccccatcctc    2040
tgccctaact acagtcgttt acctggtgct gcgtcttgct tttggtttcc agctggagaa    2100
aagaagacaa gaaagtcttg ggcatgaagg agcttttgc atctagtggg tgggaggggt    2160
caggtgtggg acatgggagc aggagactcc actttcttcc tttgtacagt aactttcaac    2220
cttttcgttg gcatgtgtgt taatccctga tccaaaaaga acaaatacac gtatgttata    2280
accatcagcc cgccagggtc agggaaagga ctcacctgac tttggacagc tggcctgggc    2340 tcccctgct caaacacagt ggggatcaga gaaaaggggc tggaaagggg ggaatggccc    2400
acatctcaag aagcaagata ttgtttgtgg tggttgtgtg tgggtgtgtg ttttttcttt    2460
ttcttctttt ttatttttt tgaatggggg aggctattta ttgtactgag agtggtgtct    2520
ggatatattc cttttgtctt catcactttc tgaaataaac ataaactgt taaaaaaaaa    2580 aaaaaaaa                                                             2588
```

<210> SEQ ID NO 150
<211> LENGTH: 2450
<212> TYPE: DNA
<213> ORGANISM: Homo sapiens
<220> FEATURE:
<221> NAME/KEY: gene
<222> LOCATION: (1)..(2450)
<223> OTHER INFORMATION: Seq2 T-bet
<220> FEATURE:
<221> NAME/KEY: mutation
<222> LOCATION: (134)..(134)
<223> OTHER INFORMATION: mutation
<220> FEATURE:
<221> NAME/KEY: mutation
<222> LOCATION: (310)..(310)
<223> OTHER INFORMATION: mutation
<220> FEATURE:
<221> NAME/KEY: misc_feature
<222> LOCATION: (952)..(970)
<223> OTHER INFORMATION: td54 bindingsite
<220> FEATURE:
<221> NAME/KEY: misc_feature
<222> LOCATION: (1096)..(1114)
<223> OTHER INFORMATION: td69 bindingsite
<220> FEATURE:
<221> NAME/KEY: misc_feature
<222> LOCATION: (1100)..(1118)
<223> OTHER INFORMATION: td70 bindingsite
<220> FEATURE:
<221> NAME/KEY: mutation
<222> LOCATION: (1399)..(1399)
<223> OTHER INFORMATION: mutation
<220> FEATURE:
<221> NAME/KEY: mutation
<222> LOCATION: (1556)..(1556)
<223> OTHER INFORMATION: mutation

<400> SEQUENCE: 150

```
cggcccgctg gagaggaagc ccgagagctg ccgcgcgcct gccggacgag ggcgtagaag      60
ccaggcgtca gagcccgggc tccggtgggg tccccaccc ggccctcggg tccccgccc      120 cctgctccct gcctatccca gcccacgcga ccctctcgcg cgcggagggg cgggtcctcg     180
```

```
acggctacgg gaaggtgcca gcccgccccg gatgggcatc gtggagccgg gttgcggaga    240
catgctgacg ggcaccgagc cgatgccggg gagcgacgag ggccgggcgc ctggcgccga    300
cccgcagcag cgctacttct acccggagcc gggcgcgcag gacgcggacg agcgtcgcgg    360
gggcggcagc ctggggtctc cctacccggg gggcgccttg gtgcccgccc cgccgagccg    420
cttccttgga gcctacgcct acccgccgcg accccaggcg gccggcttcc ccggcgcggg    480
cgagtccttc ccgccgcccg cggacgccga gggctaccag ccgggcgagg gctacgccgc    540
cccggacccg cgcgccgggc tctacccggg gccgcgtgag gactacgcgc tacccgcggg    600
actggaggtg tcggggaaac tgagggtcgc gctcaacaac cacctgttgt ggtccaagtt    660
taatcagcac cagacagaga tgatcatcac caagcaggga cggcggatgt tcccattcct    720
gtcatttact gtggccgggc tggagcccac cagccactac aggatgtttg tggacgtggt    780
cttggtggac cagcaccact ggcggtacca gagcggcaag tgggtgcagt gtggaaaggc    840
cgagggcagc atgccaggaa accgcctgta cgtccacccg gactccccca acacaggagc    900
gcactggatg cgccaggaag tttcatttgg gaaactaaag ctcacaaaca caaggggggc    960
gtccaacaat gtgacccaga tgattgtgct ccagtccctc cataagtacc agccccggct   1020
gcatatcgtt gaggtgaacg acggagagcc agaggcagcc tgcaacgctt ccaacacgca   1080
tatctttact ttccaagaaa cccagttcat tgccgtgact gcctaccaga atgccgagat   1140
tactcagctg aaaattgata taacccccct tgccaaagga ttccgggaga actttgagtc   1200
catgtacaca tctgttgaca ccagcatccc ctcccccgcct ggacccaact gtcaattcct   1260
tgggggagat cactactctc ctctcctacc caaccagtat cctgttccca gccgcttcta   1320
ccccgacctt cctggccagg cgaaggatgt ggttccccag gcttactggc tgggggcccc   1380
ccgggaccac agctatgggg ctgagtttcg agcagtcagc atgaagcctg cattcttgcc   1440
ctctgcccct gggcccacca tgtcctacta ccgaggccag gaggtcctgg cacctggagc   1500
tggctggcct gtggcacccc agtaccctcc caagatgggc ccggccagct ggttcagccc   1560
tatgcggact ctgcccatgg aacccggccc tggaggctca gagggacggg gaccagagga   1620
ccagggtccc cccttggtgt ggactgagat tgcccccatc cggccggaat ccagtgattc   1680
aggactgggc gaaggagact ctaagaggag gcgcgtgtcc ccctatcctt ccagtggtga   1740
cagctcctcc cctgctgggg cccttctcc ttttgataag gaagctgaag acagttttta   1800
taactatttt cccaactgag cagatgacat gatgaaagga acagaaacag tgttattagg   1860
ttggaggaca ccgactaatt tgggaaacgg atgaaggact gagaaggccc ccgctccctc   1920
tggccccttct ctgtttagta gttggttggg gaagtggggc tcaagaagga ttttggggtt   1980
caccagatgc ttcctggccc acgatgaaac ctgagagggg tgtccccttg ccccatcctc   2040
tgccctaact acagtcgttt acctggtgct gcgtcttgct tttggtttcc agctggagaa   2100
aagaagacaa gaaagtcttg ggcatgaagg agcttttgc atctagtggg tgggaggggt   2160
caggtgtggg acatgggagc aggagactcc actttcttcc tttgtacagt aactttcaac   2220
cttttcgttg gcatgtgtgt taatccctga tccaaaaaga acaaatacac gtatgttata   2280
accatcagcc cgccagggtc agggaaagga ctcacctgac tttggacagc tggcctgggc   2340
tccccctgct caaacacagt ggggatcaga gaaaaggggc tggaaagggg ggaatggccc   2400
acatctcaag aagcaagata ttgtttgtgg tggttgtgtg tgggtgtgtg             2450
```

<210> SEQ ID NO 151
<211> LENGTH: 2399

<212> TYPE: DNA
<213> ORGANISM: Homo sapiens
<220> FEATURE:
<221> NAME/KEY: gene
<222> LOCATION: (1)..(2399)
<223> OTHER INFORMATION: Sequenz_1 GATA-3

<400> SEQUENCE: 151

| | | | | | |
|---|---|---|---|---|---|
| ggcgccgtct | tgatactttc | agaaagaatg | cattccctgt | aaaaaaaaaa | aaaaaatact | 60 |
| gagagaggga | gagagagaga | gaagaagaga | gagagacgga | gggagagcga | gacagagcga | 120 |
| gcaacgcaat | ctgaccgagc | aggtcgtacg | ccgccgcctc | ctcctcctct | ctgctcttcg | 180 |
| ctacccaggt | gacccgagga | gggactccgc | ctccgagcgg | ctgaggaccc | cggtgcagag | 240 |
| gagcctggct | cgcagaattg | cagagtcgtc | gccccttttt | acaacctggt | cccgttttat | 300 |
| tctgccgtac | ccagtttttg | gattttttgtc | ttcccccttct | tctctttgct | aaacgacccc | 360 |
| tccaagataa | ttttaaaaa | accttctcct | ttgctcacct | ttgcttccca | gccttcccat | 420 |
| ccccccaccg | aaagcaaatc | attcaacgac | ccccgaccct | ccgacggcag | gagccccccg | 480 |
| acctcccagg | cggaccgccc | tccctccccg | cgcgcgggtt | ccgggccgg | cgagagggcg | 540 |
| cgagcacagc | cgaggccatg | gaggtgacgg | cggaccagcc | gcgctgggtg | agccaccacc | 600 |
| accccgccgt | gctcaacggg | cagcacccgg | acacgcacca | cccgggcctc | agccactcct | 660 |
| acatggacgc | ggcgcagtac | ccgctgccgg | aggaggtgga | tgtgcttttt | aacatcgacg | 720 |
| gtcaaggcaa | ccacgtcccg | ccctactacg | gaaactcggt | cagggccacg | gtgcagaggt | 780 |
| accctccgac | ccaccacggg | agccaggtgt | gccgcccgcc | tctgcttcat | ggatccctac | 840 |
| cctggctgga | cggcggcaaa | gccctgggca | gccaccacac | cgcctccccc | tggaatctca | 900 |
| gccccttctc | caagacgtcc | atccaccacg | gctccccggg | gccctctcc | gtctaccccc | 960 |
| cggcctcgtc | ctcctccttg | tcgggggggcc | acgccagccc | gcacctcttc | accttcccgc | 1020 |
| ccacccccgcc | gaaggacgtc | tccccggacc | catcgctgtc | cacccaggc | tcggccggct | 1080 |
| cggcccggca | ggacgagaaa | gagtgcctca | agtaccaggt | gccctgccc | gacagcatga | 1140 |
| agctggagtc | gtcccactcc | cgtggcagca | tgaccgccct | gggtggagcc | tcctcgtcga | 1200 |
| cccaccaccc | catcaccacc | tacccgccct | acgtgcccga | gtacagctcc | ggactcttcc | 1260 |
| cccccagcag | cctgctgggc | ggctcccccca | ccggcttcgg | atgcaagtcc | aggcccaagg | 1320 |
| cccggtccag | cacagaaggc | agggagtgtg | tgaactgtgg | ggcaacctcg | accccactgt | 1380 |
| ggcggcgaga | tggcacggga | cactacctgt | gcaacgcctg | cgggctctat | cacaaaatga | 1440 |
| acggacagaa | ccgcccctcc | attaagccca | agcgaaggct | gtctgcagcc | aggagagcag | 1500 |
| ggacgtcctg | tgcgaactgt | cagaccacca | caaccacact | ctggaggagg | aatgccaatg | 1560 |
| gggaccctgt | ctgcaatgcc | tgtgggctct | actacaagct | tcacaatatt | aacagacccc | 1620 |
| tgactatgaa | gaaggaaggc | atccagacca | gaaaccgaaa | aatgtctagc | aaatccaaaa | 1680 |
| agtgcaaaaa | agtgcatgac | tcactggagg | acttcccccaa | gaacagctcg | tttaacccgg | 1740 |
| ccgccctctc | cagacacatg | tcctccctga | gccacatctc | gcccttcagc | cactccagcc | 1800 |
| acatgctgac | cacgcccacg | ccgatgcacc | cgccatccag | cctgtccttt | ggaccacacc | 1860 |
| accccctccag | catggtcacc | gccatgggtt | agagccctgc | tcgatgctca | cagggccccc | 1920 |
| agcgagagtc | cctgcagtcc | ctttcgactt | gcattttgc | aggagcagta | tcatgaagcc | 1980 |
| taaacgcgat | ggatatatgt | ttttgaaggc | agaaagcaaa | attatgtttg | ccactttgca | 2040 |
| aaggagctca | ctgtggtgtc | tgtgttccaa | ccactgaatc | tggaccccat | ctgtgaataa | 2100 |

```
gccattctga ctcatatccc ctatttaaca gggtctctag tgctgtgaaa aaaaaaatgc      2160
tgaacattgc atataactta tattgtaaga aatactgtac aatgacttta ttgcatctgg      2220
gtagctgtaa ggcatgaagg atgccaagaa gtttaaggaa tatgggagaa atagtgtgga      2280
aattaagaag aaactaggtc tgatattcaa atggacaaac tgccagtttt gtttcctttc      2340
actggccaca gttgtttgat gcattaaaag aaaataaaaa aagaaaaaa gagaaaaga       2399

<210> SEQ ID NO 152
<211> LENGTH: 2365
<212> TYPE: DNA
<213> ORGANISM: Homo sapiens
<220> FEATURE:
<221> NAME/KEY: gene
<222> LOCATION: (1)..(2365)
<223> OTHER INFORMATION: Sequenz_2 GATA-3

<400> SEQUENCE: 152
tcccagcctt ccatccccc caccgaaagc aaatcattca acgaccccg accctccgac        60 ggcaggagcc cccgacctc ccaggcggac cgcccttccc tccccgcgcg ggttccgggc      120
ccggcgagag ggcgcgacga cagccgaggc catggaggtg acggcggacc agccgcgctg      180
ggtgagccac caccaccccg ccgtgctcaa cgggcagcac ccggacacgc accacccggg      240
cctcagccac tcctacatgg acgcggcgca gtacccgctg ccggaggagg tggatgtgct      300
ttttaacatc gacggtcaag gcaaccacgt cccgccctac tacggaaact cggtcagggc      360
cacggtgcag aggtaccctc cgacccacca cgggagccag gtgtgccgcc cgcctctgct      420
tcatggatcc ctaccctggc tggacggcgg caaagccctg gcagccacc acaccgcctc      480 cccctggaat ctcagcccct tctccaagac gtccatccac cacggctccc cggggcccct      540
ctccgtctac ccccggcct cgtcctcctc cttgtcgggg ggccacgcca gcccgcacct      600
cttcaccttc ccgcccaccc cgccgaagga cgtctccccg gacccatcgc tgtccacccc      660
aggctcggcc ggctcggccc ggcaggacga gaaagagtgc ctcaagtacc aggtgccccc      720
gcccgacagc atgaagctgg agtcgtccca ctccgtggc agcatgaccg ccctgggtgg      780
agcctcctcg tcgacccacc accccatcac cacctacccg ccctacgtgc ccgagtacag      840
ctccggactc ttcccccccca gcagcctgct gggcggctcc cccaccggct cggatgcaa      900 gtccaggccc aaggcccggt ccagcacagg caggagtgt gtgaactgtg ggcaacctc      960 gaccccactg tggcggcgag atggcacggg acactacctg tgcaacgcct gcgggctcta     1020
tcacaaaatg aacggacaga accggcccct cattaagccc aagcgaaggc tgtctgcagc     1080
caggagagca gggacgtcct gtgcgaactg tcagaccacc acaaccacac tctggaggag     1140
gaatgccaat ggggaccctg tctgcaatgc ctgtgggctc tactacaagc ttcacaatat     1200
taacagaccc ctgactatga agaaggaagg catccagacc agaaaccgaa aaatgtctag     1260
caaatccaaa aagtgcaaaa aagtgcatga ctcactggag gacttcccca agaacagctc     1320
gtttaacccg gccgccctct ccagacacat gtcctccctg agccacatct cgcccttcag     1380
ccactccagc cacatgctga ccacgcccac gccgatgcac ccgccatcca gcctgtcctt     1440
tggaccacac caccccctcca gcatggtcac cgccatgggt tagagccctg ctcgatgctc     1500
acagggcccc cagcgagagt ccctgcagtc cctttcgact tgcattttg caggagcagt      1560 atcatgaagc ctaaacgcga tggatatatg ttttgaagg cagaaagcaa aattatgttt      1620
gccactttgc aaaggagctc actgtggtgt ctgtgttcca accactgaat ctggaccca      1680 tctgtgaata agccattctg actcatatcc cctatttaac agggtctcta gtgctgtgaa     1740
```

-continued

```
aaaaaaaaat cctgaacatt gcatataact tatattgtaa gaaatactgt acaatgactt    1800
tattgcatct gggtagctgt aaggcatgaa ggatgccaag aagtttaagg aatatgggag    1860
aaatagtgtg gaaattaaga agaaactagg tctgatattc aaatggacaa actgccagtt    1920
ttgtttcctt tcactggcca cagttgtttg atgcattaaa agaaataaa aaaagaaaa     1980 aagagaaaag aaaaaaaaag aaaaagttg taggcgaatc atttgttcaa agctgttggc    2040
cctctgcaaa ggaaatacca gttctgggca atcagtgtta ccgttcacca gttgccattg   2100
agggtttcag agagccttt tctaggccta catgctttgt gaacaagtcc ctgtaattgt     2160
tgtttgtatg tataattcaa agcaccaaaa taagaaaaga tgtagattta tttcatcata    2220
ttatacagac cgaactgttg tataaattta tttactgcta gtcttaagaa ctgctttctt    2280
tcgtttgttt gtttcaatat tttccttctc tctcaatttt cggttgaata aactagatta   2340
cattcagttg gcaaaaaaaa aaaaa                                          2365
```

<210> SEQ ID NO 153
<211> LENGTH: 2728
<212> TYPE: DNA
<213> ORGANISM: Homo sapiens
<220> FEATURE:
<221> NAME/KEY: gene
<222> LOCATION: (1)..(2728)
<223> OTHER INFORMATION: Sequenz_3 GATA-3
<220> FEATURE:
<221> NAME/KEY: mutation
<222> LOCATION: (57)..(57)
<223> OTHER INFORMATION: mutation
<220> FEATURE:
<221> NAME/KEY: mutation
<222> LOCATION: (59)..(59)
<223> OTHER INFORMATION: mutation
<220> FEATURE:
<221> NAME/KEY: mutation
<222> LOCATION: (69)..(69)
<223> OTHER INFORMATION: mutation
<220> FEATURE:
<221> NAME/KEY: misc_feature
<222> LOCATION: (909)..(927)
<223> OTHER INFORMATION: hgd40 bindingsite

<400> SEQUENCE: 153

```
ggcgccgtct tgatactttc agaaagaatg cattccctgt aaaaaaaaaa aaaaaaaat    60 actgagagag ggagagagag agaagaagag agagagacgg agggagagcg agacagagcg   120
agcaacgcaa tctgaccgag caggtcgtac gccgccgcct cctcctcctc tctgctcttc   180
gctacccagg tgacccgagg agggactccg cctccgagcg gctgaggacc ccggtgcaga   240
ggagcctggc tcgcagaatt gcagagtcgt cgcccctttt tacaacctgg tcccgtttta   300
ttctgccata cccagttttt ggattttgt cttcccttc ttctctttgc taaacgaccc     360
ctccaagata attttttaaaa aaccttctcc tttgctcacc tttgcttccc agccttccca   420 tcccccccacc gaaagcaaat cattcaacga ccccgacccc tccgacggca ggagccccc   480 gacctcccag gcggaccgcc ctccctcccc gcgcgcgggt tccgggcccg gcgagagggc   540
gcgagcacag ccgaggccat ggaggtgacg gcggaccagc cgcgctgggt gagccaccac   600
caccccgccg tgctcaacgg gcagcacccg gacacgcacc acccgggcct cagccactcc   660
tacatggacg cggcgcagta cccgctgccg gaggaggtgg atgtgctttt taacatcgac   720
ggtcaaggca accacgtccc gccctactac ggaaactcgg tcaggccac ggtgcagagg    780 taccctccga cccaccacgg gagccaggtg tgccgcccgc ctctgcttca tggatcccctc   840
```

| | |
|---|---|
| cctggctgga cggcggcaaa gccctgggca gccaccacac cgcctccccc tggaatctca | 900 |
| gccccttctc caagacgtcc atccaccacg gctccccggg gccccctctcc gtctaccccc | 960 |
| cggcctcgtc ctcctccttg tcgggggggcc acgccagccc gcacctcttc accttcccgc | 1020 |
| ccaccccgcc gaaggacgtc tccccggacc catcgctgtc caccccaggc tcggccggct | 1080 |
| cggcccggca ggacgagaaa gagtgcctca agtaccaggt gcccctgccc gacagcatga | 1140 |
| agctggagtc gtcccactcc cgtggcagca tgaccgccct gggtggagcc tcctcgtcga | 1200 |
| cccaccaccc catcaccacc tacccgccct acgtgcccga gtacagctcc ggactcttcc | 1260 |
| cccccagcag cctgctgggc ggctccccca ccggcttcgg atgcaagtcc aggcccaagg | 1320 |
| cccggtccag cacagaaggc agggagtgtg tgaactgtgg ggcaacctcg accccactgt | 1380 |
| ggcggcgaga tggcacggga cactaccctgt gcaacgcctg cgggctctat cacaaaatga | 1440 |
| acggacagaa ccggcccctc attaagccca agcgaaggct gtctgcagcc aggagagcag | 1500 |
| ggacgtcctg tgcgaactgt cagaccacca caaccacact ctggaggagg aatgccaatg | 1560 |
| gggaccctgt ctgcaatgcc tgtgggctct actacaagct tcacaatatt aacagacccc | 1620 |
| tgactatgaa gaaggaaggc atccagacca gaaaccgaaa aatgtctagc aaatccaaaa | 1680 |
| agtgcaaaaa agtgcatgac tcactggagg acttccccaa gaacagctcg tttaacccgg | 1740 |
| ccgccctctc cagacacatg tcctccctga gccacatctc gcccttcagc caccccagcc | 1800 |
| acatgctgac cacgcccacg ccgatgcacc cgccatccag cctgtccttt ggaccacacc | 1860 |
| acccctccag catggtcacc gccatgggtt agagccctgc tgatgctcac agggccccca | 1920 |
| gcgagagtcc ctgcagtccc tttcgacttg cattttttgca ggagcagtat catgaagcct | 1980 |
| aaacgcgatg gatatatgtt tttgaaggca gaaagcaaaa ttatgcttgc cactttgcaa | 2040 |
| aggagctcac tgtggtgtct gtgttccaac cactgaatct ggaccccatc tgtgaataag | 2100 |
| ccattctgac tcatatcccc tatttaacag ggtctctagt gctgtgaaaa aaaaaaatgc | 2160 |
| tgaacattgc atataactta tattgtaaga aatactgtac aatgacttta ttgcatctgg | 2220 |
| gtagctgtaa ggcatgaagg atgccaagaa gtttaaggaa tatgggagaa atagtgtgga | 2280 |
| aattaagaag aaactaggtc tgatattcaa atggacaaac tgccagtttt gtttcctttc | 2340 |
| actggccaca gttgtttgat gcattaaaag aaaataaaaa aagaaaaag agaaaagaaa | 2400 |
| aaaaaagaaa aaagttgtag gcgaatcatt tgttcaaagc tgttggcctc tgcaaaggaa | 2460 |
| ataccagttc gggcaatcag tgttaccgtt caccagttgc cattgagggt ttcagagagc | 2520 |
| cttttttctag gcctacatgc tttgtgaaca agtccctgta attgttgttt gtatgtataa | 2580 |
| ttcaaagcac caaaataaga aaagatgtag atttatttca tcatattata cagaccgaac | 2640 |
| tgttgtataa atttatttac tgctagtctt aagaactgct ttctttcgtt tgtttgtttc | 2700 |
| aatatttttcc ttctctctca attttcgg | 2728 |

<210> SEQ ID NO 154
<211> LENGTH: 15
<212> TYPE: DNA
<213> ORGANISM: Artificial Sequence
<220> FEATURE:
<223> OTHER INFORMATION: katalytic domain of 10-23 type DNAzyme
<220> FEATURE:
<221> NAME/KEY: misc_feature
<222> LOCATION: (1)..(15)
<223> OTHER INFORMATION: katalytic domain of 10-23 type DNAzyme

<400> SEQUENCE: 154

| | |
|---|---|
| ggctagctac aacga | 15 |

```
<210> SEQ ID NO 155
<211> LENGTH: 33
<212> TYPE: DNA
<213> ORGANISM: Artificial Sequence
<220> FEATURE:
<223> OTHER INFORMATION: 10-23 type DNAzyme in
<220> FEATURE:
<221> NAME/KEY: misc_feature
<222> LOCATION: (1)..(33)
<223> OTHER INFORMATION: 10-23 type DNAzyme
<220> FEATURE:
<221> NAME/KEY: misc_feature
<222> LOCATION: (1)..(9)
<223> OTHER INFORMATION: a or g or c or t
<220> FEATURE:
<221> NAME/KEY: misc_feature
<222> LOCATION: (25)..(33)
<223> OTHER INFORMATION: a or g or c or t

<400> SEQUENCE: 155
nnnnnnnnng gctagctaca acgannnnnn nnn                                   33
```

METHOD FOR DIAGNOSING A MOLECULAR PHENOTYPE OF A PATIENT SUFFERING FROM AN ILLNESS ACCOMPANIED BY CHRONIC INFLAMMATION

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Incorporated by reference in its entirety is a sequence listing in computer-readable form submitted concurrently herewith and identified as follows: ASCII (text) file named "49433_SeqListing.txt," 59,470 bytes, created on Mar. 10, 2015.

BACKGROUND OF THE INVENTION

The invention relates to a method and a kit for diagnosing a molecular phenotype of a patient suffering from an illness accompanied by chronic inflammation as well as a medicament for treating such a patient.

Chronic inflammations constitute an increasing medical problem area of high socioeconomic significance. This includes in particular the following groups of illnesses: autoimmune diseases and diseases from the area of rheumatic diseases (manifestations among others on the skin, lungs, kidneys, vascular system, nervous system, connective tissue, locomotor system, endocrine system), immediate-type allergic reactions and asthma, chronic obstructive lung diseases (COPD), arteriosclerosis, psoriasis and contact eczema and chronic rejection reactions after organ and bone marrow transplants. Many of these diseases are showing a rising prevalence in the last decades not only in industrial nations, but sometimes around the world. For example, in Europe, North America, Japan and Australia more than 20% of the population suffers from allergic diseases and asthma. Chronic obstructive lung diseases are currently the fifth most frequent cause of death throughout the world and according to calculations of the WHO they will represent the third most frequent cause of death in the year 2020. Arteriosclerosis with the secondary diseases of cardiac infarction, stroke and peripheral arterial disease leads the world in morbidity and mortality statistics. Together with neurodermatitis, psoriasis and contact eczema are in general the most frequent chronic inflammatory diseases of the skin.

Due to the interactions between environmental factors and a genetic disposition, which are to date only poorly understood, there are sustained dysregulations of the immune system. In this connection the following common principles can be established for these different diseases:

(A) An excessive immune response to what are ordinarily harmless antigens for human beings. These antigens can be components of the environment (e.g. allergens such as pollen, animal hairs, food, mites, chemical substances such as preservatives, dyestuffs, detergents). In these cases patients develop an allergic reaction. In the case of e.g. active and passive smokers, chronic pulmonary lung diseases (COPD) develop. On the other hand, the immune system can also react against components of its own organism, recognize them as foreign and initiate an inappropriate inflammatory response. In these cases an autoimmune illness develops. In any case, harmless, non-toxic antigens are erroneously as foreign or dangerous and an inappropriate inflammatory response is set in motion.

(B) The diseases run in phases, including initiation, progression of the inflammatory response and the associated destruction and reconstruction with loss of organ functionality (so-called remodeling).

(C) The diseases show patient-specific sub-phenotypic manifestations.

(D) Components of the innate and acquired immunity have a sustained involvement in the initiation, maintenance and destructive and remodeling processes. Under the influence of the innate immunity (important components: antigen-presenting cells with their diverse populations and the complement system) there is an activation and differentiation of the cells of the adaptive immune system (important components: T and B lymphocytes)>The T cells take over central functions in the further course by differentiating in highly specialized effectors.

In this connection they activate and acquire certain effector mechanisms, including, in particular the following functions: antibody production: control of the functionality of effector cells of the immune system (e.g. such as neutrophilic, basophilic, eosinophilic granulocytes), feedback to functions of the innate immune system, influencing of the functionality of non-hematopoietic cells such as e.g. epithelial, endothelial, connective tissue, bones and cartilage and above all neuronal cells. Here there is a special interaction between immune and nervous systems, from which the concept of neuro-immunological interaction in the case of chronic inflammations developed.

Since the T cells, which have already been mentioned, take over central functions in the course of the disease, an understanding of their specialization is critical. A complex signal transduction cascade is involved in the differentiation of naïve $CD4^+$ cells to Th1 or Th2 cells.

The stimulation via the T cell receptor through the corresponding peptide MHC complex induces clonal expansion and programmed differentiation of $CD4^+$ T lymphocytes to T helpers (Th) 1 or Th2 cells. The differentiation of these two sub-types occurs on the basis of their cytokine profiles. Th1 cells produce interferon-$^\gamma$ ($INF^\gamma$), interleukin 2 (IL-2) and tumor-necrosis-factor-$\alpha$, while Th2 cells secrete IL-4, IL-5, IL-9 and IL-13. Bacterial and viral infections induce an immune response which is dominated by Th1 cells. On the other hand Th2 cells regulate igE production against parasites. In the process there is a balance between Th1 and Th2 cells. The destruction of this balance causes diseases, so an excessive Th1 cell response is associated with autoimmunity diseases, while allergic diseases are at the basis of a reinforced Th2 cell response.

It is known that Th1 cytokines are involved in the pathogenesis of autoimmune diseases such as e.g. autoimmune uveitis, experimental allergic encephalomyelitis, type 1 diabetes mellitus or Crohn's disease, while Th12 cytokines (IL-4, IL-5, IL-13 or IL-9) are involved in the development of chronic inflammatory respiratory ailments, such as e.g. airway eosinophilia, asthma, mucus hypersecretion and airway hyperresponsiveness. These diseases are brought about by pathophysiological changes during the production of characteristic cytokines by antigen-specific Th cells. Th2 cell sub-populations in the lungs and the airways cause the characteristic symptoms of bronchial asthma in the animal model Among other things, two transcription factors are involved in the development of autoimmune diseases and chronic inflammatory reactions: the Th1 cell-specific transcription factor Tbet and the Th2 cell-specific transcription factor GATA-3.

The Th1 cell-specific transcription factor Tbet is primarily responsible for the differentiation of naïve CD4+ T cells to Th1 cells. Its expression is controlled via the signal transduction pathways of the T cell receptor (TZR) and via INF$^\gamma$ receptor/STAT1. Tbet transactivates the endogenous INF$^\gamma$ gene and induces INF$^\gamma$ production. The in vivo function of Tbet is confirmed in knock-out mice (Tbet−/−). The quantity of Th2 cytokines is increased in mice that are deficient in Tbet.

The function of Tbet in mucosal T cells is known in the development of inflammatory bowel diseases. The transcription factor Tbet specifically induces the development of Th1 cells and controls the INF$^\gamma$ production in these cells. Through the inhibition of Tbet the balance between Th1 and Th2 cells is shifted in favor of the Th2 cells.

Many inflammatory diseases on the other hand, such as allergic asthma for example, are associated with an activation of Th2 cells. Th2 cells have an essential function in the development of allergic diseases, in particular various asthma ailments. The differentiation of Th0 cells to Th2 cells necessary for this is dependent on the transcription factor GATA-3. GATA-3 is a member of the GATA family of transcription factors.

The Th2 cell-specific transcription factor GATA-3 is primarily responsible for the differentiation of naïve CD4+ T cells to Th2 cells. In the process, the Th2 cell differentiation is primarily controlled by two signal transmission pathways, the T cell receptor (TZR) and the IL-4 receptor pathway: Signals forwarded from TZR activate the Th2 cell-specific transcription factors cMaf and GATA-3 as well as also the transcription factors NFAT and AP-1. The activation of the IL-4 receptor results in the binding of STAT6 on the cytoplasmic domain of the IL-4 receptor, where it is phosphorylated by Jak1 and Jak3 kinases. The phosphorylation for its part results in the dimerization and translocation of STAT6 to the nucleus, where STAT6 activates the transcription of GATA-3 and other genes. GATA-3 is a zinc finger transcription factor which is expressed exclusively in mature Th2 cells, not in Th1 cells.

Th2 cells produce cytokines such as for example IL-4, IL-5, IL-6, IL-13 and GM-CSF. The polarization to Th2 inhibits a Th1 differentiation through suppression of Tbet and vice versa. However, the expression of GATA-3 is not restricted to T cells. An expression of GATA-3 was also able to be confirmed in eosinophilic and basophilic granulocytes, mast cells and epithelial cells. GATA-3 plays a central role in the immunopathogenesis of chronic inflammatory diseases, in particular of allergic asthma.

Established preparations for the treatment of chronic inflammatory diseases are among others Corticosteroids, anti-leukotrienes, immunosuppressives and Anti-IgE monoclonal antibodies. Asthma patients however respond with varying degrees of success to these therapeutic agents. For a long time the question of what these differences in effectiveness were to be attributed to has remained unresolved. As a consequence, the appropriate therapy had to be fine-tuned on the patient more or less in accordance with the principle of "trial and error".

However, only recently was it determined that patients suffering from asthma, for example, could be further divided into subgroups (Woodruff et al., 2009, T-helper Type 2-driven inflammation Defines Major Subphenotypes of Asthma, Am J RespiCrit Care Med, Vol 180, 388-395). Thus, it was shown that there are at least two sub-groups of asthma patients, which were designated as "Th2 high" and "Th2 low". The subgroup "Th2 high" in the process has an increased expression of the POSTN gene, which codes for the protein periostin, as well as the genes for IL-3 and IL-5. The group "Th2 low" of tested asthma patients shows a low POSTN gene expression, comparable to a control group of healthy persons. These differing molecular phenotypes could be one cause for the different effectiveness of common therapeutic agents. Thus for the subgroup "Th2 high" an improved treatment response to treatment with corticosteroids was determined.

It was also found that two groups of asthma patients, namely "Th2 high" and "Th2 low", respond with varying degrees of success differently to a therapy with a humanized monoclonal antibody to IL-13 (Corren et al., 2011, Lebrikizumab Treatment in Adults with Asthma, The New England Journal of Medicine, 10.1056/NEJMoa 1106469). In the process, an empirical classification of asthma patients in the group "Th2 high" occurred first, when the values for serum-IgE were higher than 100 IU/ml and the number of eosinophilic granulocytes was at $0.14 \times 10^9$ cells per liter or greater. With corresponding values below these patients were placed in the group "Th2 low". Alternatively, there was a classification by the serum periostin level, which serves as a surrogate marker for Th2 cytokine IL-13, which is difficult to establish in blood or airway samples. In the process, the fact that IL-13 among others induces in vitro the expression of the periostin coding gene POSTN in epithelial cells (Woodruff et al., 2007, Proc Natl Acad Sci USA, 104(40): 15858-63. Genome-wide profiling identifies epithelial cell genes associated with asthma and with treatment response to corticosteroids). In accordance with Corren et al., 2011, patients with a serum periostin level above the average were placed in a "periostin high" group. For the mentioned sub-groups "Th2 high" and "Periostin high" a better treatment response to treatment with Anti-IL-13 antibodies by tendency was described.

According to WO 2009/124090 A1, a certain classification of asthma patients is likewise proposed, wherein the gene expression of a plurality of candidate genes, such as for example POSTN, CLCA1 and SERPINB2 is employed. Since it is known that this gene is highly regulated by the Th2 cytokine IL4 or IL-13, the cluster is also referred to as "IL-4/IL-13 signature". Along with the measurement of the serum periostin level as well as the corresponding mRNA quantity, in the process a determination of the values for serum IgE and the number of eosinophilic granulocytes were also described.

One disadvantage of patient stratification on the basis of this gene expression, above all of POSTN, is the fact that along with an "IL-4/IL-13 signature", the cytokine IL-5 also plays a significant role in the genesis of asthma. In addition, the role of the protein periostin in the immune cascade and thus the pathogenesis is unknown.

Thus the problem arises of finding a biomarker that is suitable for reliable and simultaneously clinically practicable molecular phenotyping of a human patient who is suffering from a disease that is accompanied by chronic inflammations in the groups "Th2 high" or "Th2 low" or "Th1 high" or "Th1 low". In addition, the patient classified in this manner should be able to be treated with a therapeutic agent that is especially effective specifically for this subgroup. The biomarker should make possible/facilitate an individual prediction about the effectiveness of a therapeutic agent with respect to a patient, in particular an asthma patient.

BRIEF SUMMARY OF THE INVENTION

In accordance with the invention, the problem is solved by a method for diagnosing a molecular phenotype of a human patient suffering from an illness accompanied by chronic inflammation, wherein the molecular phenotype is selected from the group consisting of the subgroups "Th2 high", "Th2 low", "Th1 high" and "Th1 low" and the gene expression of GATA-3 and/or Tbet is measured in a biological isolate of the patient and used for the assignment to a molecular phenotype of the illness. The more detailed classification of a human patient suffering from an illness accompanied by chronic inflammation occurs in the process by measurement of the gene expression of the transcription factor GATA-3 and/or of the transcription factor Tbet. As explained initially, the Th1 cell-specific transcription factor Tbet and the Th2 cell-specific transcription factor GATA-3 are involved in the development of autoimmune illnesses and chronic inflammation reactions. The polarization to Th2 inhibits a Th1 differentiation through suppression of Tbet and vice versa. Depending on the expression level of GATA-3 and/or Tbet an assignment to a molecular phenotype, that is, to a subgroup of the illness accompanied by chronic inflammation, can take place. With the inventive diagnostic method the mentioned molecular phenotyping can be performed without difficulties in a routine clinical setting with a high degree of predictability.

The transcription factors GATA-3 and Tbet are the central key molecules in the development of Th1 or Th2 dependent chronic inflammatory diseases. Therefore, the direct measurement of the protein or mRNA expression represents best possible patient stratification approach since no interconnected mechanisms can possible falsify the results.

In accordance with one preferred embodiment of the method, the expression level of GATA-3 and/or Tbet is determined via the protein or mRNA quantity. In the process, the protein quantity can be quantitatively determined with the help of an immunoassay. The immunoassay is preferably an enzyme-linked immunosorbent assay (ELISA) test, a radioimmunoassay (RIA), an electrochemiluminescence (ECL) immunoassay, a CLIA (chemoluminescence-linked immunosorbent assay), an FLIA (fluorescence-linked immunosorbent assay) or a multiplex-assay.

Along with high sensitivity and specificity, the mentioned assays offer the advantage of a potential automation and are thus particularly well suited for daily clinical practice. Of course, if necessary any other suitable test for quantitative determination of the protein quantity of GATA-3 and/or Tbet can be selected within the scope of the present invention. Furthermore, the expression level of GATA-3 and/or Tbet can occur via mass spectrometric methods, chromatographic methods such as gas chromatography, fluid-based methods with solid phase separation, such as HPLC, or microfluidic and nanofluidic methods.

The method for determining the expression of GATA-3 or Tbet with the help of an ELISA test can if necessary comprise the following:
  Production of a lysate through cell disruption;
  Addition of the lysate to a recess of a microwell plate which is coated with a first GATA-3 or Tbet specific antibody
  Washing the microwell plate;
  Addition of a second GATA-3 or Tbet specific antibody to the recess of the microwell
  Washing the microwell plate
  Detection and quantification of the GATA-3 or Tbet protein.

For the purpose of detection, the second specific antibody can for example be marked with biotin and a separate addition of an enzyme coupled to streptavidin can take place. However, the second specific antibody can also be directly coupled to an enzyme. If appropriate, a third antibody directed toward the second specific antibody can be used that is coupled to an enzyme.

The enzyme is preferably a peroxidase or alkaline phosphatase and is implemented with a suitable substrate that is suitable for colorimetry or chemiluminescence and the like.

In accordance with a further aspect of the present invention, the mRNA quantity of GATA-3 and/or Tbet can be determined additionally or as an alternative to the mentioned determination of the protein quantity. Preferably a PCR, particularly preferably a qPCR or a micro-array chip is suitable for this purpose. A person skilled in the art is aware of how to select GATA-3 and Tbet specific probes or primers for the mentioned detection methods.

In accordance with a preferred design of the method, the biological isolate was obtained whole blood, urine, sputum, a bronchial alveolar lavage (BAL), a biopsy, a brush biopsy, liquor, tracheal secretion, seminal fluid, ascitic fluid, saliva, punctate or lymph fluid. A person skilled in the art is familiar with the routine methods for obtaining suitable biological isolate.

GATA-3 and Tbet are proteins which, as transcription factors, have their effect in the cell core of T helper cells of the subtype Th1 and T1h2. In order to determine the concentration of these two nuclear proteins in a specified volume of a biological isolate, as in a specified volume of whole blood or the like, cells which form GATA-3 and Tbet must first be isolated and subsequently lyzed. A direct confirmation of these proteins from human serum or plasma is hardly possible, since they are not available there in detectable concentration. An analysis of GATA-3 and Tbet therefore takes place if necessary in four stages:
  Partitioning and isolation of the GATA-3/Tbet expressing cells from the other cellular components of the whole blood
  Disruption of the cells and release of the intracellular/nuclear proteins
  Measurement of the concentration of GATA-3 and Tbet and
  Standardization of the found concentrations of GATA-3 and Tbet.

According to an advantageous development, regardless of whether the expression level of GATA-3 and/or Tbet is determined via the protein or mRNA quantity, the inventive method comprises also one or more of the following steps:
  (i) Isolation of leukocytes, preferably by means of Ficoll gradient centrifugation;
  (ii) Enrichment of leukocytes, preferably by means of size exclusion filtration or
  (iii) Enrichment of Th1/Th2 cells in particular $CD4^+$ T cells with the help of cell-specific antibodies which are preferably coupled to magnetic beads.

The mentioned steps (i)-(iii) are performed prior to the cell disruption and in each case facilitate an increase in the sensitivity as well as predictability of the diagnostic method, since, in particular in the leukocytes the genes GATA-3 and Tbet are differentially expressed.

According to a further aspect of the present invention an assignment of the patient to a molecular phenotype of the subgroup "Th2 high" occurs when at least one of the following conditions is fulfilled:
  a) The GATA-3 gene expression in the biological isolate is higher than a defined reference value
  b) The ratio of GATA-3:Tbet gene expression in the biological isolate is higher than a defined reference value.

The subgroup "Th2 high" is thus characterized either by a high absolute GATA-3 gene expression in comparison to a defined reference value. In the process,—in the case of the measurement of the protein quantity—a corresponding value of the GATA-3 protein content in the isolate of a healthy person can be used as a reference value. However, absolute reference values can also be used. In the case of the measurement of the mRNA quantity a corresponding value of the GATA-3 mRNA quantity in the isolate of a healthy person can be used as a reference value. However, on the other hand, absolute reference values such as for example copies/ml can also be used.

An assignment of the patient to the mentioned molecular phenotype of the subgroup "Th2 high" takes place according to an advantageous embodiment of the inventive method when as an alternative to or in addition to the increased GATA-3 gene expression the ratio of GATA-3:Tbet gene expression in the biological isolate is higher than a defined reference value. In the process a corresponding value of the ratio of GATA-3:Tbet gene expression in the isolate of a healthy person is used. The determination of the ratio of GATA-3:Tbet gene expression increases the certainty of the statement, since in the process along with the GATA-3 gene expression the Tbet gene expression is established as an additional parameter. Since the two transcription factors mutually regulate one another in their expression, as initially described, the inclusion of Tbet constitutes an internal control for the measurement of the GATA-3 gene expression.

According to one advantageous development, the inventive method for assigning the patient to the molecular phenotype of the subgroup "Th2 high" comprises the steps:
  Release of proteins or RNA from cells of a biological isolate of the patient;
  Determination of the expression level of the proteins or of the mRNA for GATA-3 and/or Tbet;
  Placement of the patient in the subgroup "Th2 high" when at least one of the foregoing conditions mentioned under a) or b) apply.

As an alternative, in addition to the mentioned determination of the GATA-3 and/or Tbet gene expression, a determination of further parameters for certain placement/classification in the subgroup "Th2 high" can take place. Thus, for example the serum IgE level and the number of eosinophilic granulocytes can be measured. An assignment to the subgroup "Th2 high" takes place additionally whenever the serum IgE level is higher than 100 IU/ml and/or the number of the eosinophilic granulocytes is $0.14 \times 10^9$ cells per liter or higher. As an alternative, if required, the concentration in nitric oxide in the exhaled air, thus a determination of the FeNO value can be performed.

Another advantageous embodiment of the inventive method relates to an assignment of the patient to a molecular phenotype of the subgroup "Th2 low" when at least one of the following conditions is fulfilled:
  a) The GATA-3 gene expression in the biological isolate is lower than a defined reference value,
  b) The ratio of GATA-3:Tbet gene expression in the biological isolate is lower than a defined reference value.

The subgroup "Th2 low" is thus characterized either by a low absolute GATA-3 gene expression in comparison to a defined reference value. In the case of the measurement of the protein quantity, in the process, a corresponding value of the GATA-3 protein content in the isolate of a healthy person can be used as a reference value. Here it should be noted that in the case of a patient of the subgroup "Th2 low" with an illness accompanied by chronic inflammations the absolute GATA-3 gene expression will regularly be higher than in an isolate of a healthy patient. However, the absolute GATA-3 gene expression can also be lower than in the case of a healthy person. In any case, the GATA-3 gene expression is also not as high as described for the subgroup "Th2 high". Consequently, an assignment of the patient to the subgroup "Th2 low" occurs when said patient's GATA-3 protein content in comparison to an isolate of a healthy person, if at all, is only moderately increased. However, fixed reference values can also be used. In the case of the measurement of the mRNA quantity, a corresponding value of the GATA-3 mRNA quantity in the isolate of a healthy person can be used as a reference value, wherein an assignment of the patient to the subgroup "Th2 low" takes place when said patient's GATA-3 mRNA quantity is lower than in a corresponding sample of a healthy person or in any event is not significantly increased. However, on the other hand fixed reference values can be used.

An assignment of the patient to the mentioned molecular phenotype of the subgroup "Th2 low" takes place according to one advantageous embodiment of the inventive method, when as an alternative to or in addition to the decreased lower GATA-3 gene expression, the ratio of GATA-3:Tbet gene expression in the biological isolate is lower than a defined reference value. In the process a corresponding value of the ratio of GATA-3:Tbet gene expression in the isolate of a healthy person can be used as a reference value. The determination of the ratio of GATA-3:Tbet gene expression also increases the certainty of the statement in this case, since in the process along with GATA-3 gene expression as an additional parameter the Tbet gene expression is determined. Since the two transcription factors mutually regulate one another in their expression, as initially described, the inclusion of Tbet constitutes an internal control for the measurement of the GATA-3 gene expression.

According to one advantageous further development the inventive method for assigning the patient to the molecular phenotype of the subgroup "Th2 low" comprises the steps:
  Release of proteins or RNA from cells of a biological isolate of the patient;
  Determination of the expression level of the proteins or of the mRNA for GATA-3 and/or Tbet;
  Placement of the patient in the subgroup "Th2 low" when at least one of the foregoing conditions mentioned under a) or b) apply.

As an alternative, in addition to the mentioned determination of the GATA-3 and/or Tbet gene expression, in turn a determination of further parameters for certain placement in the subgroup "Th2 low" can take place. Thus, for example the serum IgE level and the number of eosinophilic granulocytes can be measured. An assignment to the subgroup "Th2 low" takes place additionally whenever the serum IgE level is lower than 100 IU/ml and/or the number of the eosinophilic granulocytes is below $0.14 \times 10^9$ cells per liter. As an alternative, if required, the concentration in nitric oxide in the exhaled air, thus a determination of the FeNO value can be performed.

According to another advantageous embodiment, an assignment of the patient to a molecular phenotype of the subgroup "Th1 high" occurs when at least one of the following conditions is fulfilled:
  a) The Tbet gene expression in the biological isolate is higher than a defined reference value,
  b) The ratio of Tbet:GATA-3 gene expression in the biological isolate is higher than a defined reference value.

The subgroup "Th1 high" is thus characterized either by a high absolute Tbet gene expression in comparison to a defined reference value. In the case of the measurement of the protein quantity, in the process, a corresponding value of the Tbet protein content in the isolate of a healthy person can be used as a reference value, wherein an assignment of the patient to the subgroup "Th1 high" takes place when said patient's Tbet protein content is increased. However, fixed reference values can also be used. In the case of the measurement of the mRNA quantity, a corresponding value of the Tbet mRNA quantity in the isolate of a healthy person can be used as a reference value, wherein an assignment of the patient to the subgroup "Th1 high" takes place when said patient's Tbet mRNA quantity is increased. However, on the other hand, fixed reference values can also be used.

An assignment of the patient to the mentioned molecular phenotype of the subgroup "Th1 high" takes place according to one advantageous embodiment of the inventive method, when as an alternative to or in addition to the decreased Tbet gene expression, the ratio of Tbet:GATA-3 gene expression in the biological isolate is higher than a defined reference value. In the process a corresponding value of the ratio of Tbet:GATA-3 gene expression in the isolate of a healthy person can be used as a reference value. The determination of the ratio of Tbet:GATA-3 gene expression also increases the certainty of the statement in this case, since in the process along with the Tbet gene expression as an additional parameter the GATA-3 gene expression is determined and the inclusion of GATA-3 constitutes an internal control for the measurement of the Tbet gene expression.

According to one advantageous development, the inventive method for assigning the patient to the molecular phenotype of the subgroup "Th1 high" comprises the steps:
  Release of proteins or RNA from cells of a biological isolate of the patient;
  Determination of the expression level of the proteins or of the mRNA for Tbet and/or GATA-3;
  Placement of the patient in the subgroup "Th1 high" when at least one of the foregoing conditions mentioned under a) or b) apply.

A further aspect of the present invention relates to a method that facilitates an assignment of the patient to a molecular phenotype of a subgroup "Th1 low" when at least one of the following conditions is fulfilled:
  a) The Tbet gene expression in the biological isolate is lower than a defined reference value,
  b) The ratio of Tbet:GATA-3 gene expression in the biological isolate is lower than a defined reference value.

The subgroup "Th1 low" is thus characterized either by a low absolute Tbet gene expression in comparison to a defined reference value. In the case of the measurement of the protein quantity, in the process, a corresponding value of the Tbet protein content in the isolate of a healthy person can be used as a reference value. Here it should be noted that in the case of a patient of the subgroup "Th1 low" with an illness accompanied by chronic inflammations the absolute Tbet gene expression can however be higher than in an isolate of a healthy person. However, the absolute Tbet gene expression can also be lower than in the case of a healthy person. In any event, the Tbet gene expression is not as high as described for the subgroup "Th1 high". Hence, an assignment of the patient to the subgroup "Th1 low" takes place when said patient's Tbet protein content in comparison to an isolate of a healthy person, if at all, is increased, however not significantly. However, fixed reference values can also be used. In the case of the measurement of the mRNA quantity, a corresponding value of the Tbet mRNA quantity in the isolate of a healthy person can be used as a reference value, wherein an assignment of the patient to the subgroup "Th1 low" takes place when said patient's Tbet mRNA quantity is lower than in the corresponding sample of a healthy patient or in any event is not significantly increased. However, on the other hand, fixed reference values can also be used.

An assignment of the patient to the mentioned molecular phenotype of the subgroup "Th1 low" takes place according to one advantageous embodiment of the inventive method, when as an alternative to or in addition to the decreased Tbet gene expression, the ratio of Tbet:GATA-3 gene expression in the biological isolate is lower than a defined reference value. In the process a corresponding value of the ratio of Tbet:GATA-3 gene expression in the isolate of a healthy person can be used as a reference value. The determination of the ratio of Tbet:GATA-3 gene expression also increases the certainty of the statement in this case, since in the process along with the Tbet gene expression as an additional parameter the GATA-3 gene expression is determined and the inclusion of GATA-3 constitutes in a certain sense an internal control for the measurement of the Tbet gene expression.

According to one advantageous development, the inventive method for assigning the patient to the molecular phenotype of the subgroup "Th1 low" comprises the steps:
  Release of proteins or RNA from cells of a biological isolate of the patient;
  Determination of the expression level of the proteins or of the mRNA for Tbet and/or GATA-3;
  Placement of the patient in the subgroup "Th1 low" when at least one of the foregoing conditions mentioned under a) or b) apply.

As an alternative, in addition to the mentioned determination of the GATA-3 and/or Tbet gene expression, in turn a determination of further parameters for certain placement in the subgroup "Th1 high" and "Th1 low" can take place. Thus, for example the number of eosinophilic granulocytes or the serum IgE level can be measured. An assignment to the subgroup "Th1 high" takes place when the serum IgE level is lower than 100 IU/ml and/or the number of the eosinophilic granulocytes is below $0.14 \times 10^9$ cells per liter. Otherwise, an assignment to the subgroup "Th1 low" takes place. As an alternative, if required, the concentration in nitric oxide in the exhaled air, thus a determination of the FeNO value can be performed.

In order to consider differences in sample preparation, a standardization of the concentrations of GATA-3 and Tbet can be performed. Differences in the sample preparation can for example come about through differing cell numbers that are lyzed, through differing lysis efficiencies of the individual samples or through differing content in the various cell types within the cell preparations. In accordance with the invention, possibilities for standardization include the following: Standardization to the total protein content of the cell lysate, standardization to the cell number that has been lyzed or standardization to the concentration of specific marker proteins that are specifically found in specified cell types.

The patients with the diagnosed molecular phenotype of the subgroup "Th2 high" can under circumstances simultaneously be placed in the subgroup "Th1 low". Also, patients with the diagnosed molecular phenotype of the subgroup "Th1 high" can under circumstances simultaneously be placed in the subgroup "Th2 low". This is to be attributed to the fact represented above that the polarization to Th2 inhibits a Th1 differentiation through suppression of Tbet and vice versa.

Within the scope of the present invention, illnesses are diagnosed or treated that are accompanied by chronic inflammations, such as autoimmune diseases and diseases from the area of rheumatic diseases (manifestations among others on the skin, lungs, kidneys, vascular system, nervous system, connective tissue, locomotor system, endocrine system), immediate-type allergic reactions and asthma, chronic obstructive lung diseases (COPD), arteriosclerosis, psoriasis and contact eczema as well as chronic rejection reactions after organ and bone marrow transplants. Also tumor diseases can be diagnosed and treated in accordance with the invention, provided GATA-3 or Tbet are involved in the development and/or deregulated as after-effects.

Within the scope of the present invention, the chronic inflammatory disease is either Th2-induced, such as for example allergic bronchial asthma, rhinoconjunctivitis, allergic sinusitis, atopical dermatitis, food allergies, pemphigus, ulcerative colitis, parasitic illnesses, or Th1-induced, such as for example psoriasis, allergic contact eczema, Crohn's disease, COPD, rheumatoid arthritis, autoimmune diseases, type 1 diabetes mellitus or MS.

The aforementioned problem is additionally solved in accordance with the invention through a medicament for the treatment of illnesses of a human patient with a molecular phenotype that are accompanied by chronic inflammations, wherein the molecular phenotype has been determined in accordance with one or more embodiments of the mentioned inventive diagnostic method. The identified molecular phenotype comprises in the process in particular the groups "Th1 low, "Th1 high", "Th2 low" or "Th2 high".

According to one preferred embodiment the mentioned medicament contains a specific ribonucleic acid or deoxyribonucleic acid specific for GATA-3 or Tbet, in particular a DNAzyme specific for GATA-3 or Tbet.

The "10-23" model represents a general DNAzyme model (Sontoro et al., 1997). DNAzymes of the 10-23 model—also referred to as "10-23 DNAzymes" have a catalytic domain of 15 nucleotides, which are flanked by two substrate binding domains. The catalytic domain in the process preferably has the sequence ggctagctacaacga (SEQ ID No. 154). The length of the substrate binding domains is variable: they are either of equal length or variable in length. In one preferred design, the length of the substrate binding domains ranges between 6 and 14 nucleotides, very especially preferably in each case at least nine nucleotides. Such DNAzymes comprise the general sequence nnnnnnnnnggctagctacaacgannnnnnnnnn (SEQ ID NO 155). Especially preferable in the process are substrate binding domains that bind the mRNA, coding for the proteins GATA-3 and Tbet.

The specified catalytic central domain ggctagctacaacga is only one preferred embodiment. A person skilled in the art is aware of the fact that "10-23 DNAzymes" can be obtained with comparable biological activity with a modified catalytic domain.

In one especially preferred embodiment, the substrate binding domains are completely complementary to the region that flanks the cleaving site. However, in order to bind the target RNA and cleave it, the DNAzyme does not necessarily have to be completely complementary. DNAzymes of the 10-23 type cleave the target mRNA on purine-pyrimidine sequences. Within the scope of the present invention the DNAzymes preferably comprise the in vivo active DNAzymes against GATA-3 and Tbet in accordance with WO 2005/033314 A2, whose content is incorporated as disclosure content of the present invention.

A medicament for specific inhibition of the GATA-3 expression in vivo contains in particular at least one DNAzyme selected from the group consisting of DNAzymes with a sequence in accordance with one of the sequences SEQ ID NO 1 through SEQ ID NO 70. Such a DNAzyme binds preferably on an mRNA which codes for a human GATA-3 gene with a gene sequence selected from the sequences SEQ ID NO 151 (human GATA-3 from database no.: XM_043124), SEQ ID NO 152 (human GATA-3 from Database No.: X58072) and SEQ ID NO 153 (human GATA-3, sequenced from plasmid pCR2.1).

A medicament for specific inhibition of the GATA-3 expression in vivo preferably contains the DNAzyme hgd40 with the sequence 5'-GTGGATGGAggctagctacaacgaGTCT-TGGAG (SEQ ID NO 40).

A medicament for specific inhibition of the Tbet expression in vivo contains in particular at least one DNAzyme selected from the group consisting of DNAzymes with a sequence according to one of the sequences SEQ ID NO 71 through SEQ ID NO 148. Such a DNAzyme preferably binds on an mRNA which codes for a human Tbet gene with a gene sequence selected from the sequences SEQ ID NO 149 (human Tbet from the Database No.: NM_013351) and SEQ ID NO 150 (human Tbet sequenced from pBluescript-SK).

A medicament for specific inhibition of the Tbet expression in vivo contains preferably the DNAzyme td69 with the sequence 5'-GGCAATGAAggctagctaccaacgaTGGGTTTCT (SEQ ID NO 139) or td70 with the sequence 5'-TCACG-GCAAggctagctacaacgaGAACTGGGT (SEQ ID No 140).

As an alternative to the DNAzymes the medicament for specific inhibition of the GATA-3 or Tbet expression can contain a suitable siRNA.

The medicament preferably has a formulation with which the mentioned specific ribonucleic acid or deoxyribonucleic acid molecules can be administered to the patient in the form of a pharmaceutically acceptable composition either orally, rectally, parenterally, intravenously, intramuscularly or subcutaneously, intracisternally, intravaginally, intraperitoneally, intrathecally, intravascularly, locally (powder, ointment or drops) or in the form of a spray. For the local administration of the medicament of this invention include ointments, powders, sprays or inhalants. The active component is mixed under sterile conditions with a physiologically acceptable excipient and possible preservatives, buffers or propellants, depending on requirements.

The medicament can be used for therapy for all diseases that are accompanied by chronic inflammations.

According to an especially preferred design of the present invention, the treatment of the patients takes place with a molecular phenotype of the subgroup "Th2 high" with a GATA-3 specific DNAzyme. The therapy of a patient with a molecular phenotype of the subgroup "Th1 high" takes place with a Tbet specific DNAzyme. In addition, the treatment of a patient with the molecular phenotype of the subgroup "Th2 low" can take place with a Tbet specific DNAzyme and the treatment of a patient with the molecular phenotype of the subgroup "Th1 low" can occur with a GATA-3 DNAzyme.

An inventive medicament with a GATA-3 specific DNAzyme is thus provided preferably for the treatment of a patient with the molecular phenotype of the subgroup "Th2 high" and a medicament with a Tbet specific DNAzyme is preferably provided for the treatment of a patient with the molecular phenotype of the subgroup "Th1 high".

In accordance with the invention, one special advantage of the medicament according to an embodiment mentioned above for the specific therapy of an inventively diagnosed subgroup of patients—namely "Th2 high", "Th2 low", "Th1 high" or "Th1 low" lies in the fact that with the help of the specific medicament, in particular of a DNAzyme and/or an siRNA, a functional inactivation of the coding ribonucleic acid molecules of transcription factors takes place, whose differential expression was determined beforehand and which is involved in the development of the chronic inflammatory reactions and autoimmune diseases. This strategy differs distinctly from conventional approaches and also differs from the approach according to Corren et al., 2011, since there, one the one hand for example the quantity of periostin (surrogate marker) is measured, but then a therapy aimed at another target, such as for example IL-13 with the help of an anti-IL13 antibody was proposed. The inventive medicament on the other hand has a high specificity. It causes a cell-specific intervention and is specific for compartments and organs.

Dosage forms of the inventive medicament comprise pharmaceutically acceptable compositions which contain modifications and "prodrugs", provided they do not trigger excessive toxicity, irritations or allergic reactions in patients according to reliable medical assessment. The term "prodrug" relates to compounds that are transformed for improvement of the absorption, such as for example through hydrolysis in the blood.

The inventive medicament can also be used in the form of a multiple emulsion for application of the mentioned specific nucleic acid molecules. A suitable multiple emulsion to this end comprises an exterior water phase W1, an oil phase O dispersed in the exterior water phase W1 and an interior water phase W2 dispersed in the oil phase O, wherein in the interior water phase W2 at least one electrolyte selected from the group of alkali metal halides and earth alkali metal halides and sulfates and at least one specific ribonucleic acid or deoxyribonucleic acid molecule, preferably a DNAzyme specific for GATA-3 or Tbet is provided, wherein the exterior water phase W1 contains a hydrophilic emulsifier which is a polymer of ethylene oxide and propylene oxide, and the oil phase O is formed by triacylglycerides and has a lipophilic emulsifier from the group of dimethicones. With the help of such multiple emulsion in particular nucleic acid molecules can be especially effectively protected from undesirable decomposition.

The type of dosage will be determined by the attending physician in accordance with the clinical factors. A person skilled in the art is aware of the fact that the type of dosage is dependent on different factors such as e.g. body size, weight, body surface, age, sex or the general health of the patient, but also depends on the agent to be administered, the duration and type of administration and on other medicaments that may be administered in parallel. In the process, according to an especially advantageous embodiment, the quantity of the active ingredient of the medicament can be adapted to the measured expression level. Thus, in the case of placement in the subgroup "Th2 high" and an established very high GATA-3 gene expression an increase dose of the active ingredient, in particular a DNAzyme specific for GATA-3 specific can be administered. Correspondingly, in the case of placement in the subgroup "Th1 high" and an established very high Tbet gene expression an increased dose of the active ingredient, in particular of a DNAzyme specific for Tbet can be administered.

A further aspect of the present invention relates to a kit for diagnosing a molecular phenotype of a human patient suffering from an illness accompanied by chronic inflammation, wherein the kit contains at least one specific component for quantitative determination of the protein or mRNA quantity of GATA-3 and/or Tbet in a biological isolate of the patient.

The inventive kit for diagnosis can be easily offered in the form of a ready to use "kit" which comprises antibodies or antigens that are adsorbed on a surface of a carrier and a preparation of human IgG antibodies which e.g. in the case of a human, a preparation of anti-human IgG antibodies that are marked such that they are proved by a cascade of reactions of the type biotin-streptavidin peroxidase or alkaline phosphatase.

As an alternative, the kit for diagnosis also comprises, in addition to a carrier, buffers and reagents, e.g. reagents which are necessary for proof of the reaction such as e.g. streptavidin that is coupled to a marker that gives a color reaction.

As an alternative, the kit additionally comprises a standard sample of GATA-3 and/or Tbet for calibration of the kit, wherein for proof of the protein or mRNA of GATA-3 and/or Tbet, a standard sample is used.

In the case of one preferred embodiment, a specific antibody against GATA-3 and/or Tbet is included for the quantitative determination of the protein quantity. If necessary, in accordance with a modification, further components for execution of an immunoassay, in particular an ELISA, can be included.

The further component for carrying out the ELISA is selected from the group consisting of lysis buffers for cell disruption, a microwell plate, protein quantity standards for GATA-3 and/or Tbet, secondary antibodies and a coupled enzyme for implementation of a substrate for detection. Preferably, in addition to a first specific antibody against GATA-3 and/or Tbet the kit comprises a further specific antibody against GATA-3 or Tbet.

The kit can contain a sequence specific probe and/or primer for the GATA-3 and/or Tbet genes for quantitative determination of the mRNA quantity.

BRIEF DESCRIPTION OF THE DRAWINGS

Further features, details and advantages of the invention arise from the wording of the claims as well as from the following description of exemplary embodiments with the assistance of the drawings. The figures show the following:

DETAILED DESCRIPTION OF THE INVENTION

Figure 1:
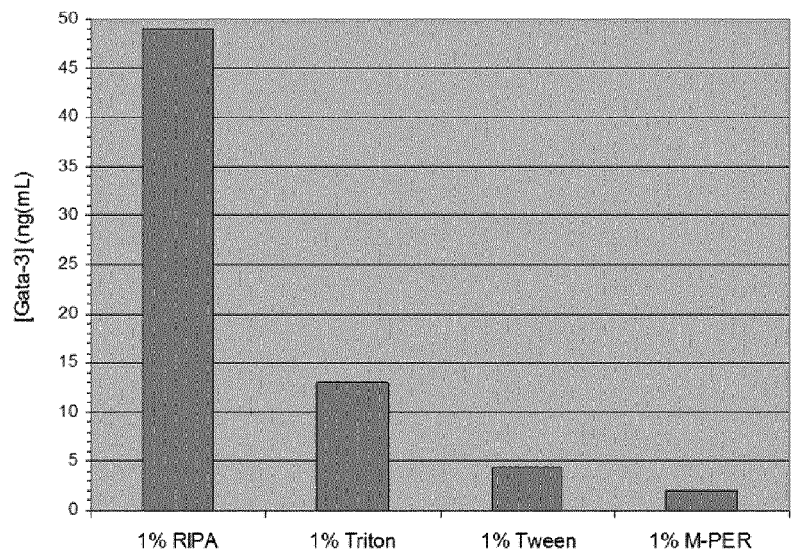
FIG. 1 shows the influence of various detergents on the release of GATA-3 from stimulated Jurkat cells, FIG. 2a,b show results of a quantification of Tbet and GATA-3 by means of chromogenic sandwich ELISA.

Material and Methods:

Cells can be isolated, for example, by means of technologies based on the binding of specific antibodies. Magnetic beads, which can be obtained from the firms Miltenyi (Macs-System), Dynal (DynaBeads) or BD-Bioscience (iMAG), are used. As an alternative this happens via a cell purification by means of fluorescent marked antibodies on cell sorters for example from the firm Cytomation (MOFLO) or BD-Bioscience (FACS-Vantage). The purity of the target cells is preferably at least 80%, more strongly preferred at least 95% and most preferred at least 99%.

Methods for the isolation of RNA are e.g. described in Sambrook and Russell, Molecular Cloning, A Laboratory Manual, 3$^{rd}$ Edition, Cold Spring Harbor Laboratory (2001), New York and Ausubel et al., Current Protocols in Molecular Biology, John Wiley & Sons (1998), New York. In addition it is possible for the average person skilled in the art to use commercially available kits (Silika-Technologie) e.g. the RNeasy Kit from the firm Qiagen, for RNA isolation. In addition it is preferable to purify mRNA directly from the target cells by using commercial kits for example from the firm Qiagen (Oligotex mRNA Kit), Promega (PolyATract mRNA Isolation System) or Miltenyi (mRNAdirect).

Exemplary Embodiments
Exemplary Embodiment 1

GATA-3 and Tbet are proteins that, as transcription factors, have their effect in the cell core of T helper cells of the subtype Th1 and Th2. In order to determine the concentration of these two nuclear proteins in a specified volume of a biological isolate in particular in a specified volume of whole blood, cells which form GATA-3 and Tbet must first be isolated and subsequently lyzed. A direct proof of these proteins from human serum or plasma is not possible, since they are not present there in detectable concentration. An analysis of GATA-3 and Tbet therefore takes place in 4 stages:

Partitioning and isolation of the GATA-3/Tbet expressing cells from the other cellular components of the whole blood Disruption of the cells and release of the intracellular/nuclear proteins Measurement of the concentration of GATA-3 and Tbet and Standardization of the found concentrations of GATA-3 and Tbet.

Partitioning and Isolation of the GATA-3/Tbet Expressing Cells from the Other Cellular Components of the Whole Blood This can be performed by different methods of variable complexity, in particular the following steps for partitioning and isolation within the scope of the present invention:

An isolation of leukocytes from whole blood by means of Ficoll density gradient centrifugation with subsequent affinity purification of the Th1/Th2 cell types by antibodies against specific surface markers, If necessary, the affinity purification of the Th1/Th2 cell types by antibodies against specific surface markers can also be performed as a 1-stage method without prior enrichment of the leukocytes, If necessary, the isolation of leukocytes through Ficoll density gradient centrifugation from whole blood suffices in order to perform a quantification of the proteins GATA-3 and Tbet, If necessary, in place of the Ficoll density gradient centrifugation a bead-based affinity purification of the Th1/Th2 cell types through antibodies against specific surface markers in a deep-well plate in the 96 well format can be employed, If required, in place of the Ficoll density gradient centrifugation a bead-based affinity purification of the leukocytes through antibodies against specific surface markers in a deep-well plate in the 96 well format can be employed, If necessary, a hypoosmolar lysis of the erythrocytes can take place to obtain a leukocyte preparation or If necessary the protein disruption can occur directly from the whole blood Disruption of the Cells and Release of the Intracellular/Nuclear Proteins This can be achieved through various methods and principles, in particular within the scope of the present invention the following procedural steps:

Destruction of cellular membranes through lysis buffers with different principles of operation:
 a) Hypotonic buffers which induce a bursting of the cells
 b) Buffers containing detergents, which destroy the cell membrane and as a result, release intracellular proteins
 c) Buffers of high ionic strength or osmotically active buffers which remove water from the cells and as a result destroy the cell integrity Physical methods such as heating up, shock freezing or ultrasound Mechanical methods such as homogenizing or grinding.

Examples of buffers containing detergents could be:

Buffer systems with a high concentration of ionic (e.g. SDS or cholate and its derivatives) or non-ionic (e.g. triton or Tween-20) detergents Mixtures of ionic and non-ionic detergents (e.g. Ripa buffers with 50 mM Tris.HCl (pH 7.5), 150 mM NaCl, 1% NP40, 0.5% sodium deoxycholate and 0.1% SDS)

Commercially available lysis buffers with unknown composition (e.g. M-PER)

The influence of different detergents on the release of GATA-3 from stimulated Jurkat cells is illustrated in FIG. 1. The lysis of Jurkat cells (human T cell line) through various lysis buffers and quantification of GATA-3 by means of ELISA resulted in an especially high release of GATA-3 protein in the case of the use of the RIPA buffer (1% RIPA). About 50 ng/ml of GATA-3 were verified.

Measurement of the Concentration of GATA-3 and Tbet

Figure 2A:
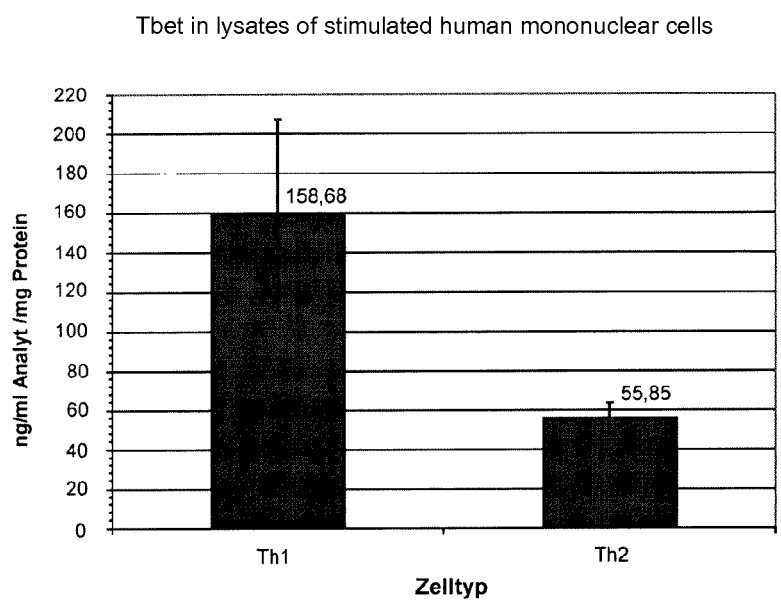
Figure 2B:
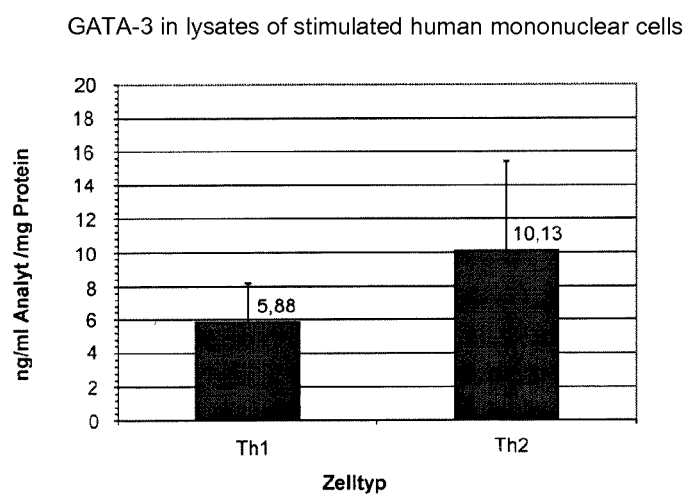

In principle, the concentration of the two transcription factors GATA-3 and Tbet can be determined with different methods. Within the scope of the present invention, among others there are:

ELISA (enzyme linked immunosorbent assay)
CLIA (chemoluminescence linked immunosorbent assay)
FLIA (fluorescence linked immunosorbent assay)
Mass spectrometric methods
Chromatographic methods (e.g. gas chromatography)
Fluid-based methods with solid phase separation, (e.g. HPLC)
Microfluidic and nanofluidic methods FIG. 2a and FIG. 2b show the results of a quantification of Tbet and GATA-3 by means of chromogenic sandwich ELISA. The cells were obtained from whole blood through Ficoll density gradient centrifugation. The cells (stimulated human mononuclear cells) were lyzed with a Ripa buffer. The lysate was examined with two ELISA prototype methods with respect to the concentration of GATA-3 and Tbet. The concentration of the two proteins was depicted with respect to the total protein concentration of the cell lysates (standardization to protein content).

The results in accordance with FIG. 2a show that Th1 cells have a higher content of Tbet (circa 160 ng/ml analyte/mg protein) than Th2 cells (circa 56 ng/ml analyte/mg protein) and this fact can be clearly confirmed from the results of the ELISA test:

| Cells | Ng/ml Tbet/mg Protein |
|---|---|
| Th2 B11-14 | 51.01 |
| Th2 B11-15 | 58.40 |
| Th2 B11-16 | 50.24 |
| Th2 B11-17 | 68.79 |
| Th2 B11-19 | 49.63 |
| Th2 B11-20 | 55.85 |
| Mean | 55.65 |
| STABW | 7.31 |
| VK (%) | 13.14 |
| Th1 B11-14 | 202.24 |
| Th1 B11-19 | 106.34 |
| Th1 B11-20 | 167.46 |
| Mean | 158.68 |
| STABW | 48.55 |
| VK (%) | 30.59 |

The Tbet content in the Th1 cells is thus more than two times greater, namely by a factor of about three, than in the Th2 cells.

According to FIG. 2b the content in GATA-3 in the Th2 cells (circa 10 ng/ml analyte/mg protein) is higher than in Th1 cells (circa 6 ng/ml analyte/mg protein) The GATA-3 content is more than 1.5 times higher in the Th2 cells here—namely by a factor of about 1.7—than in Th1 cells.

In addition, one can see from FIGS. 2a and 2b that in the case of standardization to the protein content the quantity ratio of Tbet:GATA-3 in Th1 cells differs significantly form the corresponding ratio in Th2 cells. Thus the quantity ratio of Tbet:GATA-3 here in Th1 cells is about 27, thus more than 20, while the corresponding quantity ratio in Th2 cells is circa 6, thus less than 10.

The quantitative determination of GATA-3 and Tbet occurs in each case by means of a sandwich ELISA (Enzyme linked immune sorbent assay).

Figure 3:
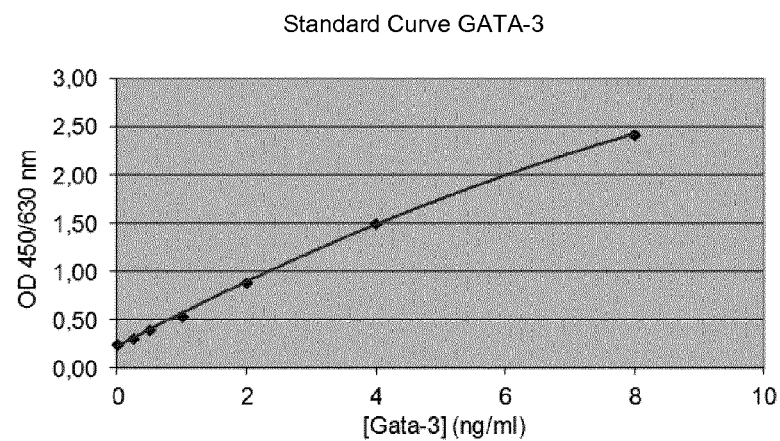
FIG. 3 shows a standard curve of a GATA-3 ELISA for quantification of samples

Exemplary Embodiment 2—GATA-3 ELISA:

To this end, the wells of a 96 well microwell plate are coated with specific antibodies against GATA-3. After addition of the sample or of a standard, GATA-3 binds on the antibodies on the 96 well plate. After a wash step to remove the non-bound substances a second, specific biotinylated antibody against GATA-3 is added. After an additional wash step to remove the non-bound substances peroxidase marked streptavidin is added. After a last wash step to remove the non-bound substances substrate is added. The color development is terminated after a defined time by adding a stop solution. The intensity of the color development is quantified by a microwell plate reader. The quantification of the samples occurs by a comparison to the included standards of known protein concentration. FIG. 3 shows a corresponding standard curve of a GATA-3 ELISA.

Figure 4:
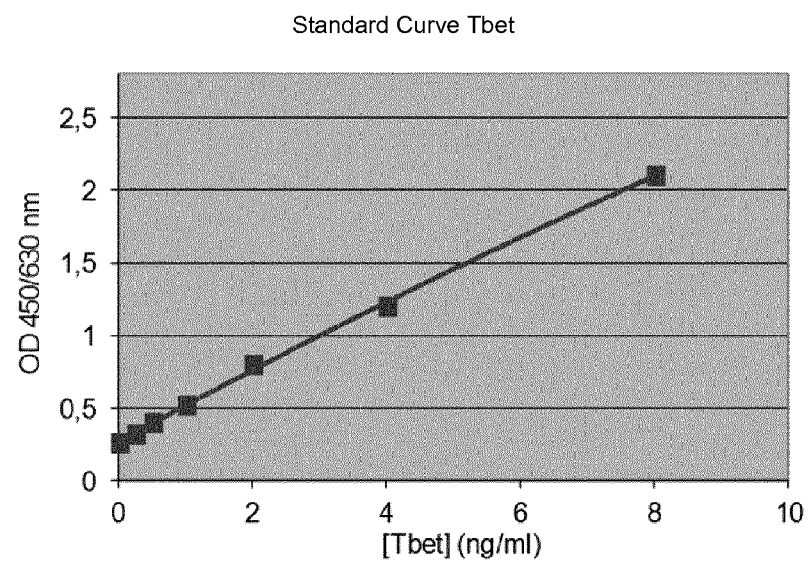
FIG. 4 shows a standard curve of a Tbet ELISA for quantification of samples

According to the exemplary embodiment for the performance of the GATA-3 ELISA, the steps relate to the following in detail:
 Insert number of required wells into a frame of the 96 well plate
 Addition of 50 µl/well assay buffer
 Addition of 100 µl/well standard/control/sample
 Incubation for 60 minutes on the shaker
 Wash all wells 4× with 400 µl/well of wash buffer
 Addition of 100 µl/well biotinylated anti-GATA-3 antibodies
 Incubation for 60 minutes on the shaker
 Wash all wells 4× with 400 µl/well of wash buffer
 Addition of 100 µl/well peroxidase marked streptavidin
 Incubation for 30 minutes on the shaker
 Wash all wells 4× with 400 µl/well of wash buffer
 Addition of 100 µl/well substrate
 Incubation for 30 minutes
 Stop reaction by addition of 100 µl stop solution
 Measurement of optical density at 450 nm with a microwell plate reader Exemplary Embodiment 3—Tbet ELISA:

The verification of the Tbet protein is executed in accordance with the following test principle: The quantitative determination of Tbet occurs by means of a sandwich ELISA (Enzyme linked immuno sorbent assay). To this end the wells of a 96 well microwell plate are coated with specific antibodies against Tbet. After addition of the sample or of a standard, Tbet binds on the antibodies on the 96 well plate. After a wash step to remove the non-bound substances a second, specific antibody against Tbet is added. After an additional wash step to remove the non-bound substances a peroxidase marked antibody against the Tbet specific antibody is added. After a last wash step to remove the non-bound substances substrate is added. The color development is terminated after a defined time by adding a stop solution. The intensity of the color development is quantified by a microwell plate reader. The quantification of the samples occurs by a comparison to the included standards of known protein concentration. FIG. 4 shows a corresponding standard curve of a Tbet ELISA.

According to the exemplary embodiment for the performance of the Tbet ELISA the steps relate to the following in detail:
 Insert number of required wells into a frame of the 96 well plate
 Addition of 50 µl/well assay buffer
 Addition of 100 µl/well standard/control/sample
 Incubation for 60 minutes on the shaker
 Wash all wells 4× with 400 µl/well of wash buffer
 Addition of 100 µl/well anti-Tbet antibodies
 Incubation for 60 minutes on the shaker
 Wash all wells 4× with 400 µl/well of wash buffer
 Addition of 100 µl/well peroxidase marked anti-Tbet specific antibodies
 Incubation for 30 minutes on the shaker
 Wash all wells 4× with 400 µl/well of wash buffer
 Addition of 100 µl/well substrate
 Incubation for 30 minutes
 Stop reaction by addition of 100 µl stop solution
 Measurement of optical density at 450 nm with a microwell plate reader Standardization of the Concentrations of GATA-3 and Tbet
 In order to consider differences in the sample preparation, a standardization of the concentrations of GATA-3 and Tbet can be performed. Differences in the sample preparation can arise e.g. due to the following:

Differing cell numbers to be lyzed

Differing lysis efficiencies of the individual samples or

Differing content in the different cell types within the cell preparations.

Possibilities for standardization include the following:

Standardization to the total protein content of the cell lysate (see under "Measurement of the Concentrations of GATA-3 and Tbet")

Standardization to the cell number being lyzed (see FIG. 5) or

Standardization to the concentration of specific marker proteins that are specifically found in specified cell types.

Figure 5:
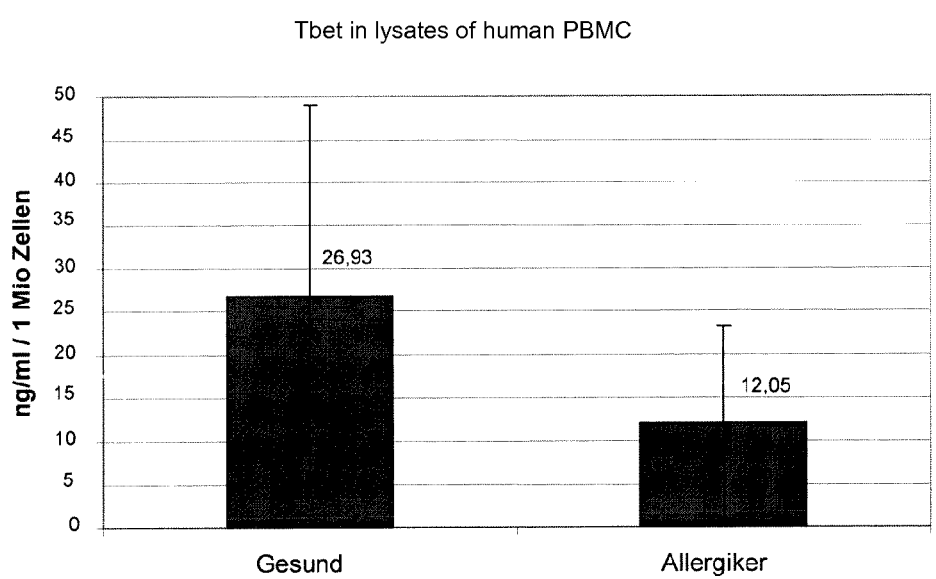
FIG. 5 shows a standardized determination of Tbet in lysates of human peripheral mononuclear cells (PBMC)

FIG. 5 shows a standardized determination of Tbet in lysates of human peripheral mononuclear cells (PBMC). In the process a lysis of PBMCs of healthy subjects and patients suffering from allergic illnesses, such as e.g. allergic bronchial asthma, rhinoconjunctivitis, allergic sinusitis, atopical dermatitis, food allergies takes place. The concentration of Tbet was standardized to the cell number in the lysates. The illness is Th2 dependent and consistently a slight concentration in Tbet (circa 12 ng/ml/1 million cells) for allergy sufferers was determined compared to healthy subjects (circa 27 ng/ml/1 million cells). The Tbet concentration was thus reduced in the case of allergy sufferers by more than a factor of 2 compared to healthy subjects. Consequently, an assignment of the patients to the molecular phenotype "Th1 low" is easily possible here, since the Tbet gene expression in the biological isolate is lower than a defined reference value, here the Tbet gene expression of healthy subjects.

Exemplary Embodiment 4

In modification of Examples 2 and 3, in accordance with Example 4 Th1/Th2 cells are enriched by means of magnetic beads coated with cell specific antibodies for the sample preparation. Subsequently the verification of GATA-3 occurred in accordance with the provision according to Example 2.

Exemplary Embodiment 5

In modification of Examples 2 and 3, in accordance with Example 4 leukocytes are enriched by means of size exclusion filtration for the sample preparation. Subsequently the verification of GATA-3 occurred in accordance with the provision according to Example 2.

Exemplary Embodiment 6

A GATA-3 specific DNAzyme shows therapeutic effects in the mouse model of the OVA induced allergic airway inflammation of the "Th2 high" phenotype.

In order to provide the best possible illustration of the clinical phenotype "Th2 high" in the mouse model BALB/c mice were sensitized with the model allergen ovalbumin (OVA) in the presence of the adjuvant Al(OH)$_3$ on days 0, 14 and 21 through intraperitoneal injection. On days 24-26 the mice inhaled a 1% OVA aerosol in order to cause a Th2 dominated allergic inflammatory reaction in the lungs. On days 23-26 the GATA-3 specific DNAzyme hgd40 (SEQ ID NO 40), dissolved in PBS, was intranasally administered. In the process the Balb/c-mouse strain is characterized in that it generates preferentially strong Th2 responses. This is reinforced by the use of AL(OH)$_3$ as an adjuvant, which distinctly supports the formation of Th2 dominated immune responses. The described mouse model is correspondingly characterized by a massive infiltration of eosinophils an Th2 cells in the airways accompanied by a hyperplasia of the mucus forming goblet cells with increased mucus production as well as the formation of an airway hyperresponsiveness. Immunologically, along with allergen specific Th2 cells, characterized by the production of the typical cytokines IL-4, IL-5 and IL-13, also OVA specific antibodies of the immune globulin classes IgE and IgG1 (in the mouse both Th2 dependent) were detectable. All these parameters are typical clinical features of a "Th2 high" phenotype (Wenzel et al., Am J Respir Crit Care Med. 199 September; 160(3):1001-8; Woodruff et al., 2009). In the process the reaction strength with respect to some parameters in the animal model were even more distinctly pronounced than in the clinical situation with human patients, e.g. eosinophilic granulocytes constitute circa 60-70% of all leukocytes in the bronchial alveolar lavage (BAL) in the mouse model, while already 3-5% of these cells in the sputum of patients indicates a Th2 dominated phenotype.

Figure 6:
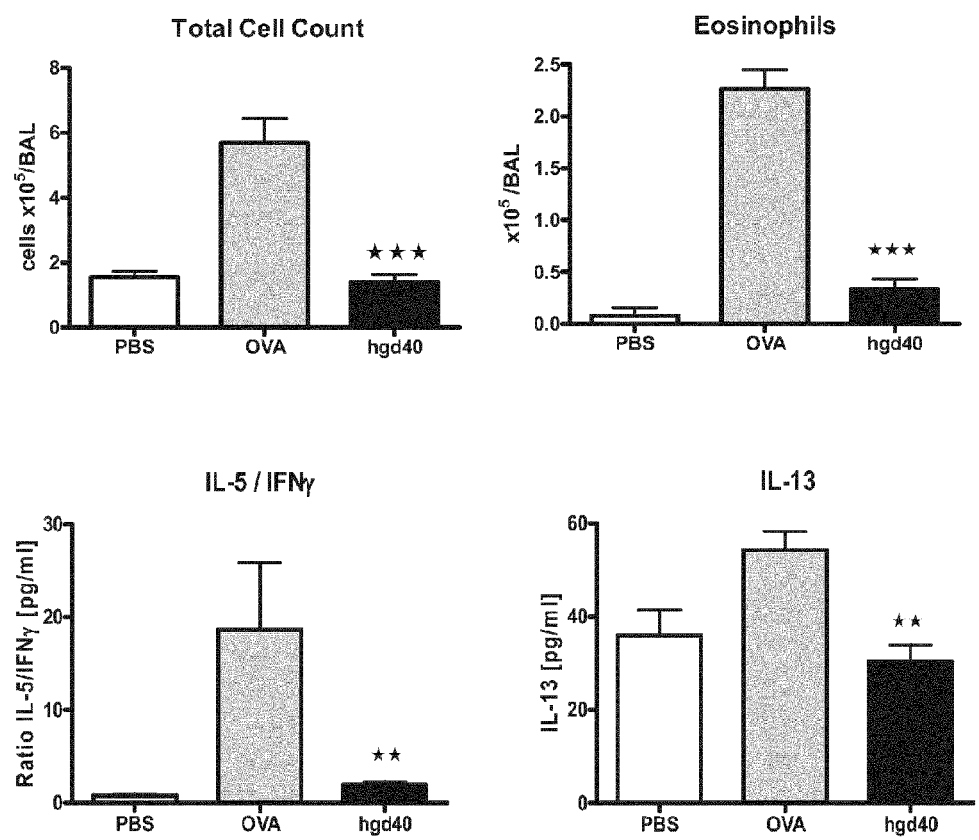
FIG. 6 shows a significant improvement of allergic airway inflammation after four-day treatment with the GATA-3 specific DNAzyme hgd40 (SEQ ID NO 40) compared to untreated mice.

According to FIG. 6, after four-day treatment with the GATA-3 specific DNYzyme hgd40 (SEQ ID NO 40) compared to untreated mice, a significant improvement of the allergic airway inflammation was ascertained. Above all the number of eosinophils in the BAL was significantly reduced. In addition, the BAL concentrations of the characteristic cytokines for the phenotype "Th2 high", IL-5 and IL-13, were able to be significantly reduced.

Exemplary Embodiment 7

A GATA-3 specific DNAzyme shows significant therapeutic effects in the chronic mouse model of a Th2 dominated allergic airway inflammation.

In order to provide the best possible illustration of the clinical phenotype "Th2 high" in the mouse model, BALB/c mice were sensitized with the model allergen ovalbumin (OVA) in the presence of the adjuvant Al(OH)$_3$ on days 0, 14 and 21 through intraperitoneal injection. By means of twice weekly OVA aerosol provocations over a time period of 14 weeks a chronic inflammation of the airways was caused in the mice. During the last eight weeks therapy was provided three times a week (until day 121) either with budesonide or the GATA-3 specific DNAzyme hgd40 through intranasal application.

Figure 7:
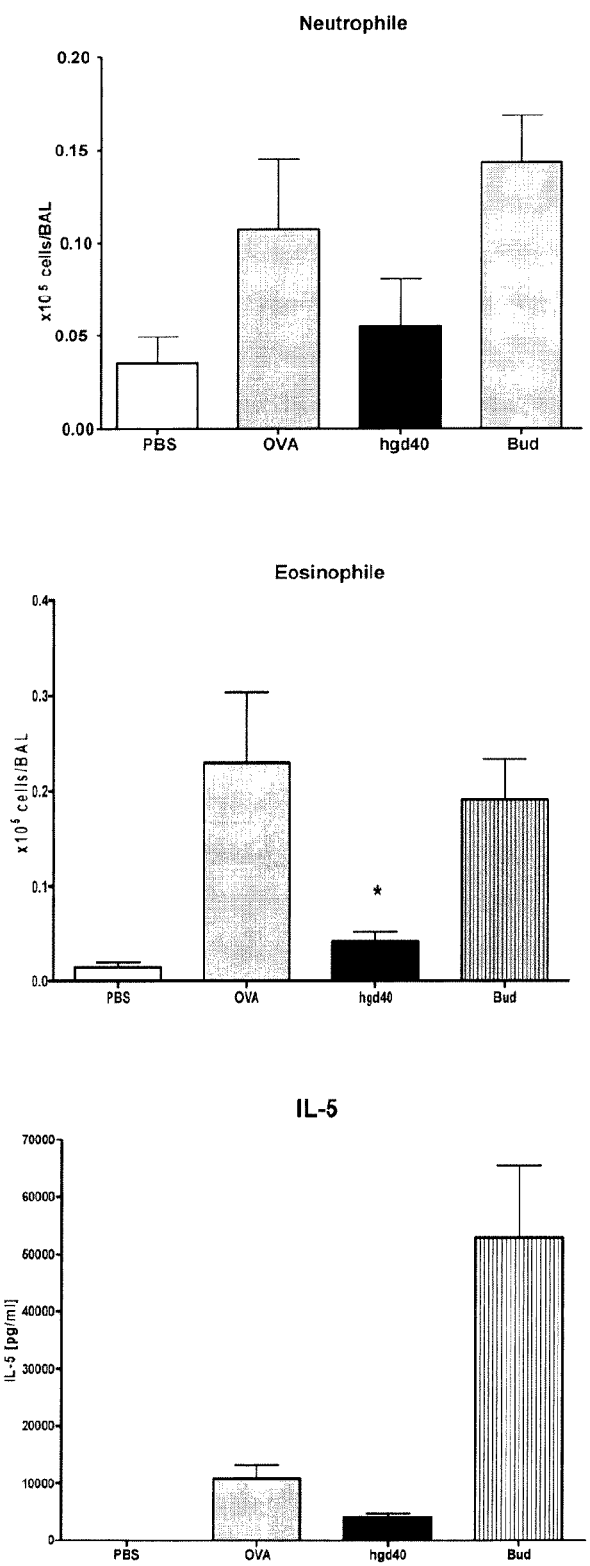
FIG. 7 shows the influence of the GATA-3 specific DNAzyme hgd40 (SEQ ID NO 40) on the number of neutrophils occurring in the chronic inflammation, the number of eosinophils in the BAL and the release of IL-5 after an eight-week treatment
Figure 8:
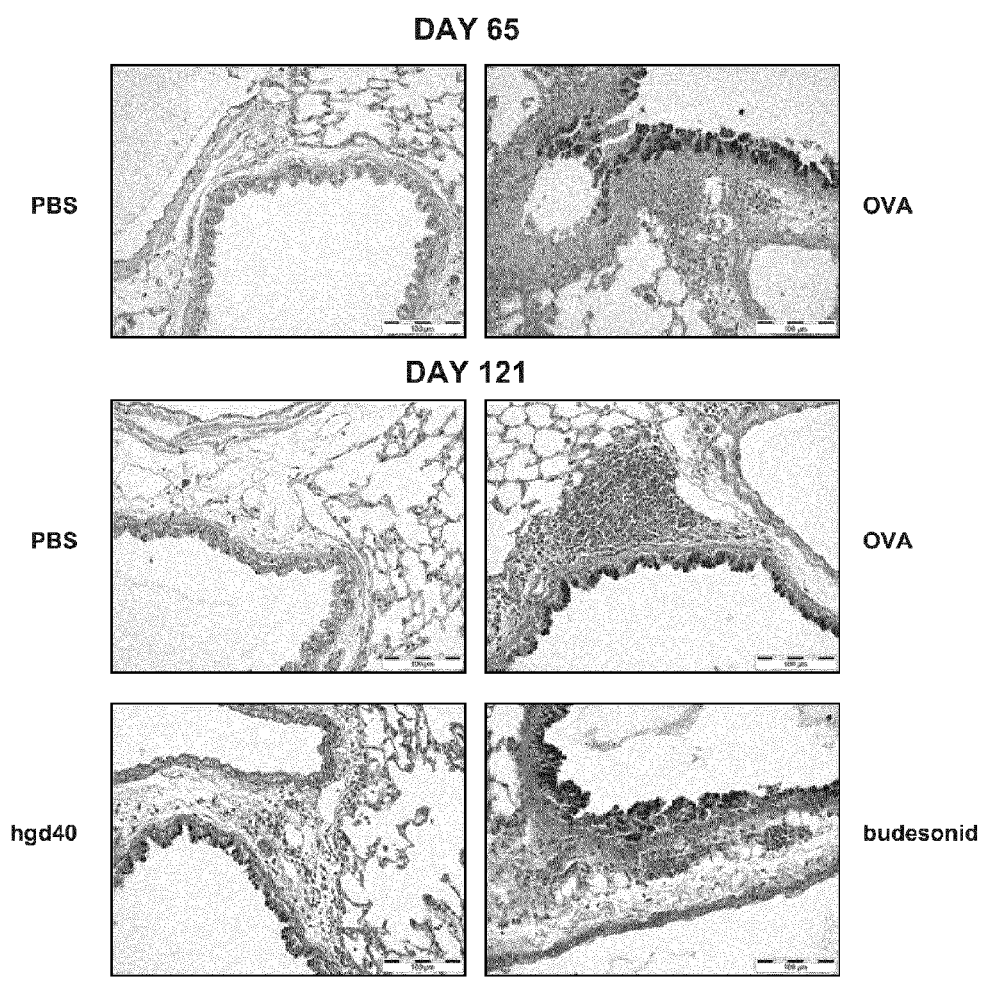
FIG. 8 shows the influence of the GATA-3 specific DNAzyme hgd40 (SEQ ID NO 40) on the peribronchial/perivascular inflammation and goblet cell hyperplasia in the lung tissue.

According to FIGS. 7 and 8 after eight weeks of treatment with GATA-3 specific DNAzyme hgd40 (SEQ ID NO 40) the number of eosinophils in the BAL was able to be significantly reduced and in addition a reduction of the number of neutrophils occurring in the chronic inflammation was also observed. This was accompanied by a lowered peribronchial/perivascular inflammation and reduced goblet cell hyperplasia. Simultaneously, in re-stimulated lymphocytes of those treated with hgd40 a reduced release of IL-5 was observed. In the budesonide group, on the other hand no significant improvement of the parameters cold be observed.

The invention is not restricted to one of the previously described embodiments, but rather can be modified in many respects.

All features and advantages arising from the claims, the description and the drawings, including design details, spatial arrangements and procedural steps can be essential to the invention both individually as well as in a variety of combinations.

We claim:

1. A method for diagnosing and treating chronic inflammation in a patient suffering from an illness associated with chronic inflammation, by identifying a molecular phenotype of the patient wherein the molecular phenotype is selected from the group consisting of the subgroups "Th2 high", and "Th2 low" and the gene expression of Th2 cell-specific transcription factor (GATA-3) and/or the Th1 cell-specific transcription factor (Tbet) is measured in a biological isolate of the patient and used for the assignment to a molecular phenotype of the illness wherein the expression level of GATA-3 and/or Tbet is determined via the protein or mRNA quantity, and wherein the protein quantity is quantitatively determined by an immunoassay and wherein a therapeutic agent effective for specifically inhibiting GATA-3 or Tbet expression according to the identified molecular phenotype is administered to the patient.

2. The method according to claim 1, characterized in that the immunoassay is selected from the group consisting of an ELISA test, a radioimmunoassay, an electrochemiluminescence immunoassay, a CLIA (chemoluminescence-linked immunosorbent assay), an FLIA (fluorescence-linked immunosorbent assay) and a multiplex-assay.

3. The method according to claim 1, characterized in that an assignment of the patient to a molecular phenotype of the subgroup "Th2 high" occurs when at least one of the following conditions is fulfilled:

the GATA-3gene expression in the biological isolate is higher than a defined reference value the ratio of GATA-3 : Tbet gene expression in the biological isolate is higher than a defined reference value.

4. The method according to claim 1, characterized in that an assignment of the patient to a molecular phenotype of the subgroup "Th2 low" occurs when at least one of the following conditions is fulfilled:

the GATA-3 gene expression in the biological isolate is lower than a defined reference value, the ratio of GATA-3 : Tbet gene expression in the biological isolate is lower than a defined reference value.

5. The method according to claim 1, characterized in that along with the determination of the gene expression of GATA-3 and/or Tbet a determination of the serum IgE level and/or the number of eosinophilic granulocytes occurs and/or the $Fe_{NO}$ value is determined.

6. The method according to claim 1, characterized in that the illness accompanied by chronic inflammations is Th2-induced, such as for example allergic bronchial asthma, rhinoconjunctivitis, allergic sinusitis, atopical dermatitis, food allergies, pemphigus, ulcerative colitzis, parasitic illnesses, or Th1-induced, such as for example psoriasis, allergic contact eczema, Crohn's disease, COPD, rheumatoid arthritis, autoimmune diseases, type 1 diabetes mellitus or MS.

* * * * *